US012709737B2

(12) United States Patent
Shen et al.

(10) Patent No.: US 12,709,737 B2
(45) Date of Patent: Aug. 18, 2026

(54) ENHANCED CHIMERIC ANTIGEN RECEPTOR CELLS IN HYPOXIC TUMOR MICROENVIRONMENT

(71) Applicants: Innovative Cellular Therapeutics Holdings, Ltd., George Town (KY); Innovative Cellular Therapeutics, Inc., Rockville, MD (US)

(72) Inventors: Xiaogang Shen, Shanghai (CN); Xudong Tang, Shanghai (CN); Chengfei Pu, Shanghai (CN); Lei Xiao, Rockville, MD (US); Le Tian, Rockville, MD (US)

(73) Assignees: Innovative Cellular Therapeutics Holdings, Ltd., George Town (KY); Innovative Cellular Therapeutics, Inc., Rockville, MD (US)

( * ) Notice: Subject to any disclaimer, the term of this patent is extended or adjusted under 35 U.S.C. 154(b) by 639 days.

(21) Appl. No.: 18/156,482

(22) Filed: Jan. 19, 2023

(65) Prior Publication Data

US 2023/0227779 A1 Jul. 20, 2023

Related U.S. Application Data

(60) Provisional application No. 63/351,200, filed on Jun. 10, 2022, provisional application No. 63/300,868, filed on Jan. 19, 2022.

(51) Int. Cl.

| | |
|---|---|
| ***C12N 5/0783*** | (2010.01) |
| ***C07K 14/54*** | (2006.01) |
| ***C07K 14/57*** | (2006.01) |
| ***C07K 16/28*** | (2006.01) |
| ***C07K 16/30*** | (2006.01) |
| ***C07K 16/40*** | (2006.01) |
| *A61K 39/00* | (2006.01) |

(52) U.S. Cl.

CPC ........ *C12N 5/0636* (2013.01); *C07K 14/5412* (2013.01); *C07K 14/5434* (2013.01); *C07K 14/5443* (2013.01); *C07K 14/57* (2013.01); *C07K 16/28* (2013.01); *C07K 16/303* (2013.01); *C07K 16/40* (2013.01); *A61K 2039/505* (2013.01); *C07K 2319/02* (2013.01); *C07K 2319/03* (2013.01); *C07K 2319/33* (2013.01); *C12N 2500/02* (2013.01); *C12N 2510/00* (2013.01)

(58) Field of Classification Search

CPC .............. C12N 5/0636; C12N 2510/00; C12N 2740/16043; C07K 14/5412; C07K 14/5434; C07K 14/5443; C07K 14/57; C07K 16/28; C07K 2319/33; C07K 14/7051; A61K 40/11; A61K 40/31; A61K 40/42

See application file for complete search history.

(56) References Cited

U.S. PATENT DOCUMENTS

| | | | |
|---|---|---|---|
| 2021/0077532 | A1 | 3/2021 | Xiao et al. |
| 2021/0137983 | A1 | 5/2021 | Xiao et al. |

FOREIGN PATENT DOCUMENTS

| | | | |
|---|---|---|---|
| CN | 108164600 | A | 6/2018 |
| WO | WO02099104 | A1 | 12/2002 |
| WO | WO2017106061 | A1 | 6/2017 |
| WO | WO2020169974 | A1 | 8/2020 |

OTHER PUBLICATIONS

Harada et al., "Antitumor Effect of TAT-oxygen-dependent Degradation-caspase-3 Fusion Protein Specifically Stabilized and Activated in Hypoxic Tumor Cells," Apr. 2002, Cancer research, 62(7):2013-2018.

Kosti et al., "Hypoxia-sensing CAR T Cells Provide Safety and Efficacy in Treating Solid Tumors," Apr. 2021, Cell Reports Medicine, 2(4):100227. 23 pages.

Extended European Search Report mailed May 22, 2023 for European Patent Application No. 23152492.7, a corresponding foreign application of U.S. Appl. No. 18/156,482, 12 pages.

He et al., "Conditioned CAR-T cells by hypoxia-inducible transcription amplification (HiTA) system significantly enhances systemic safety and retains antitumor efficacy," Journal for Immunotherapy of Cancer, Aug. 2021, 9(10): e002755m, 17 pages.

Liao et al., "Engineering T cells with hypoxia-inducible chimeric antigen receptor (HiCAR) for selective tumor killing," Biomarker Research, Oct. 2020, 8:56, 5 pages.

*Primary Examiner* — Jeremy C Flinders
*Assistant Examiner* — Masudur Rahman
(74) *Attorney, Agent, or Firm* — Lee & Hayes, P.C.

(57) ABSTRACT

Embodiments of the present disclosure relate to compositions and methods of enhancing lymphocytes' ability to treat cancer patients. Embodiments relate to a polynucleotide comprising a nucleic acid encoding a chimeric antigen receptor (CAR), a nucleic acid encoding an Oxygen-Dependent Degradation domain (ODD), and a nucleic acid encoding one or multiple sequences of Hypoxia-Response Element (HRE).

19 Claims, 8 Drawing Sheets

Specification includes a Sequence Listing.

killing 24H luciferase assay

Specific lysis(%)

0
20
40
60
80

NT
6004
6023
6024

20% O2
0.1% O2
1% O2
3% O2
5% O2

175: CLDN 18.2 scFv

| Reference | Construct |
|---|---|
| 6004 | 175-bbz-wpre mut6 |
| 6023 | LV-9X HRE-EF1a-175-BBZ-ODD domain |
| 6024 | LV-9X HRE-EF1a-175-BBZ-miniODD domain |

FIG. 4

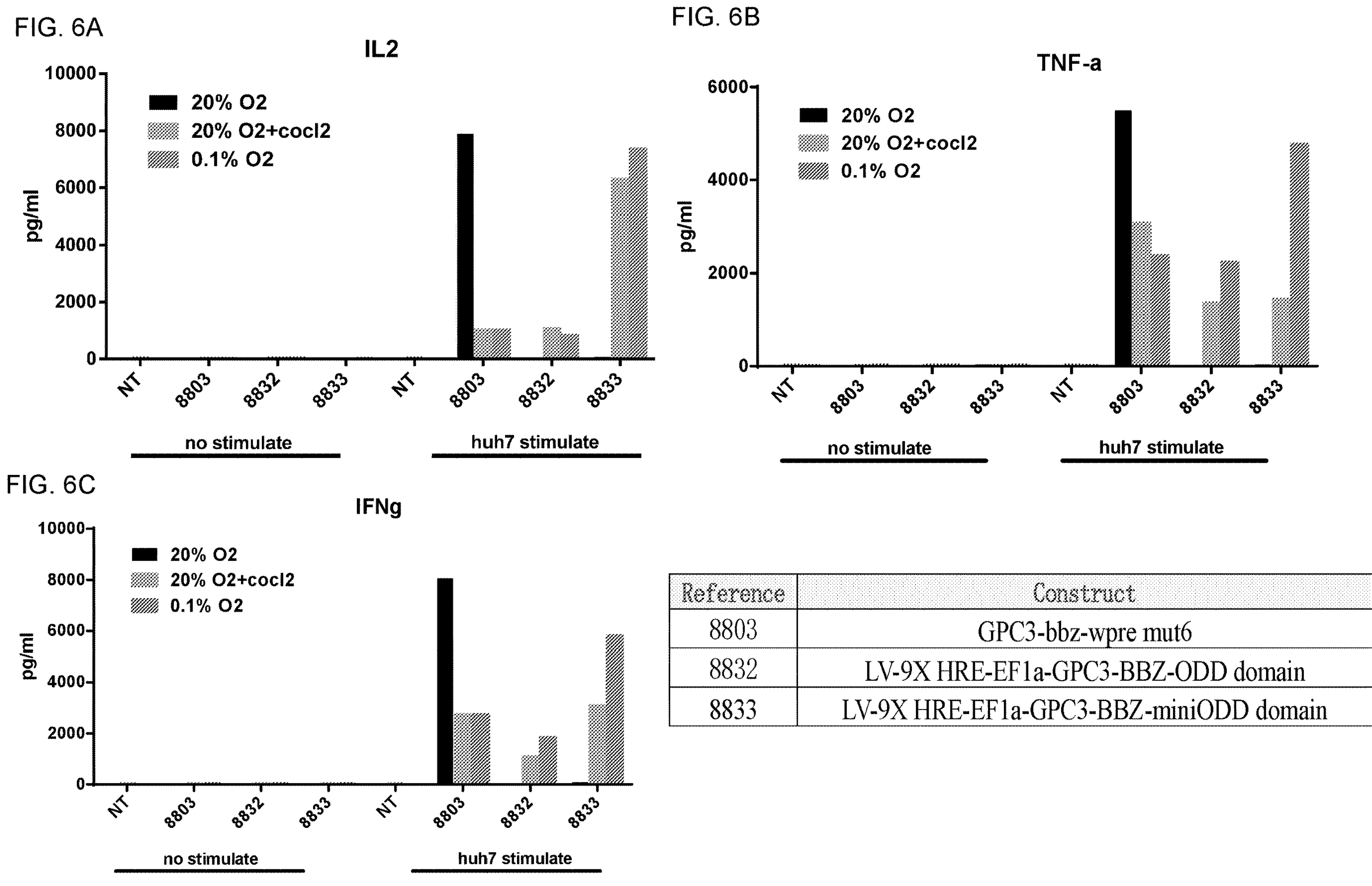
| Reference | Construct |
|---|---|
| 8803 | GPC3-bbz-wpre mut6 |
| 8832 | LV-9X HRE-EF1a-GPC3-BBZ-ODD domain |
| 8833 | LV-9X HRE-EF1a-GPC3-BBZ-miniODD domain |

| Reference | Construct |
| --- | --- |
| 6701 | GUCY2C-bbz |
| 6755 | LV-9X HRE-EF1a-5F9-BBZ-ODD domain |
| 6756 | LV-9X HRE-EF1a-5F9-BBZ-miniODD domain |

IL2
pg/ml
6000
4000
2000
0
20% O2
0.1% O2
1% O2
3% O2
7% O2
NT
6701
6755
6756

TNF-a
pg/ml
2000
1500
1000
500
0
20% O2
0.1% O2
1% O2
3% O2
7% O2
NT
6701
6755
6756

IFNg
pg/ml
5000
4000
3000
2000
1000
0
20% O2
1% O2
3% O2
7% O2
NT
6701
6755
6756

GZMB
pg/ml
15000
10000
5000
0
20% O2
1% O2
3% O2
7% O2
NT
6701
6755
6756

SEQUENCE LISTING

```
Sequence total quantity: 27
SEQ ID NO: 1            moltype = DNA  length = 306
FEATURE                 Location/Qualifiers
source                  1..306
                        mol_type = genomic DNA
                        organism = Homo sapiens
SEQUENCE: 1
ggccctacgt gctgtctcac acagcctgtc tgacggccct acgtgctgtc tcacacagcc  60
tgtctgacgg ccctacgtgc tgtctcacac agcctgtctg acggccctac gtgctgtctc  120
acacagcctg tctgacggcc ctacgtgctg tctcacacag cctgtctgac ggccctacgt  180
gctgtctcac acagcctgtc tgacggccct acgtgctgtc tcacacagcc tgtctgacgg  240
ccctacgtgc tgtctcacac agcctgtctg acggccctac gtgctgtctc acacagcctg  300
tctgac                                                              306

SEQ ID NO: 2            moltype = DNA  length = 113
FEATURE                 Location/Qualifiers
source                  1..113
                        mol_type = genomic DNA
                        organism = Homo sapiens
SEQUENCE: 2
cattttgaca cccccataat atttttccag aattaacagt ataaattgca tctcttgttc  60
aagagttccc tatcactctc tttaatcact actcacagta acctcaactc ctg         113

SEQ ID NO: 3            moltype = DNA  length = 63
FEATURE                 Location/Qualifiers
source                  1..63
                        mol_type = genomic DNA
                        organism = Homo sapiens
SEQUENCE: 3
atggcgctgc cggtgaccgc gctgttactg ccgctggcgc tgttactgca cgccgcgcgc  60
ccg                                                                63

SEQ ID NO: 4            moltype = AA  length = 21
FEATURE                 Location/Qualifiers
source                  1..21
                        mol_type = protein
                        organism = Homo sapiens
SEQUENCE: 4
MALPVTALLL PLALLLHAAR P                                            21

SEQ ID NO: 5            moltype = DNA  length = 735
FEATURE                 Location/Qualifiers
source                  1..735
                        mol_type = other DNA
                        organism = synthetic construct
SEQUENCE: 5
gaaatcgtgc tgacgcagag tccggcgacc ctgagcttaa gcccgggcga acgcgcgacg  60
ctgagctgcc gcgcgagcga aagcgtggat aactatggcc tgagctttat taactggttt  120
cagcagaaac cgggccaagc gccgcgcctg ctgatttatg gcacgagcaa ccgcggcagc  180
ggcattccgg cgcgctttag cggcagcggt agtggcaccg attttaccct gaccattagc  240
agcctggaac cggaagattt tgcggtgtat ttttgtcagc agagcaacga agtgccgtat  300
acctttggcg gtggcaccaa agtggaaatt aaaggcggtg gtggtagcgg tggtggcggt  360
agcggcggcg gtggcagcca agtgcagctg gtgcagagcg gcgcggaagt gaaaaaaccg  420
ggcgcgagcg tgaaagtgag ctgcaaagcg agcggctata ccctgaccga ttataacatg  480
gattgggtgc gccaagcgcc gggccaaggc ctggaatgga ttggcgatat ttatccgaac  540
accggcggca ccatttataa tcagaaattt aaaggccgcg tgaccatgac cattgatacg  600
agcacgagca ccgtgtatat ggaactgagc agcctgcgca gcgaagatac cgcggtgtat  660
tattgcaccc gctttcgcgg cattcattat gcgatggatt attggggcca aggcaccacc  720
gtgaccgtga gcagc                                                   735

SEQ ID NO: 6            moltype = AA  length = 245
FEATURE                 Location/Qualifiers
source                  1..245
                        mol_type = protein
                        organism = synthetic construct
```

```
SEQUENCE: 6
EIVLTQSPAT LSLSPGERAT LSCRASESVD NYGLSFINWF QQKPGQAPRL LIYGTSNRGS  60
GIPARFSGSG SGTDFTLTIS SLEPEDFAVY FCQQSNEVPY TFGGGTKVEI KGGGGSGGGG  120
SGGGGSQVQL VQSGAEVKKP GASVKVSCKA SGYTLTDYNM DWVRQAPGQG LEWIGDIYPN  180
TGGTIYNQKF KGRVTMTIDT STSTVYMELS SLRSEDTAVY YCTRFRGIHY AMDYWGQGTT  240
VTVSS                                                              245

SEQ ID NO: 7           moltype = DNA  length = 669
FEATURE                Location/Qualifiers
source                 1..669
                       mol_type = genomic DNA
                       organism = Homo sapiens
SEQUENCE: 7
accacgacgc cagcgccgcg accaccaaca ccggcgccca ccatcgcgtc gcagcccctg  60
tccctgcgcc cagaggcgtg ccggccagcg gcggggggcg cagtgcacac gagggggctg  120
gacttcgcct gtgatatcta catctgggcg cccttggccg ggacttgtgg ggtccttctc  180
ctgtcactgg ttatcaccct ttactgcaaa cggggcagaa agaaactcct gtatatattc  240
aaacaaccat ttatgagacc agtacaaact actcaagagg aagatggctg tagctgccga  300
tttccagaag aagaagaagg aggatgtgaa ctgagagtga agttcagcag gagcgcagac  360
gcccccgcgt accagcaggg ccagaaccag ctctataacg agctcaatct aggacgaaga  420
gaggagtacg atgttttgga caagaggcgt ggccgggacc ctgagatggg gggaaagccg  480
agaaggaaga accctcagga aggcctgtac aatgaactgc agaaagataa gatggcggag  540
gcctacagtg agattgggat gaaaggcgag cgccggaggg gcaaggggca cgatggcctt  600
taccagggtc tcagtacagc caccaaggac acctacgacg cccttcacat gcaggccctg  660
ccccctcgc                                                          669

SEQ ID NO: 8           moltype = AA  length = 223
FEATURE                Location/Qualifiers
source                 1..223
                       mol_type = protein
                       organism = Homo sapiens
SEQUENCE: 8
TTTPAPRPPT PAPTIASQPL SLRPEACRPA AGGAVHTRGL DFACDIYIWA PLAGTCGVLL  60
LSLVITLYCK RGRKKLLYIF KQPFMRPVQT TQEEDGCSCR FPEEEEGGCE LRVKFSRSAD  120
APAYQQGQNQ LYNELNLGRR EEYDVLDKRR GRDPEMGGKP RRKNPQEGLY NELQKDKMAE  180
AYSEIGMKGE RRRGKGHDGL YQGLSTATKD TYDALHMQAL PPR                    223

SEQ ID NO: 9           moltype = DNA  length = 612
FEATURE                Location/Qualifiers
source                 1..612
                       mol_type = genomic DNA
                       organism = Homo sapiens
SEQUENCE: 9
gcgccggcgg cgggcgatac cattattagc ctggattttg gcagcaacga taccgaaacc  60
gatgatcagc agctggaaga agtgccgctg tataacgatg tgatgctgcc gagcccgaac  120
gaaaaactgc agaacattaa cctggcgatg agcccgctgc caacggccga aaccccgaaa  180
ccgttacgca gcagcgcgga tccggcgctg aaccaagaag tggcgctgaa actggaaccg  240
aacccggaaa gcctggaact gagctttacc atgccgcaga ttcaagatca gaccccgagc  300
ccgagcgatg gcagcacccg tcagagcagc ccggaaccga acagcccgag cgaatattgc  360
ttttatgtgg atagcgatat ggtgaacgaa tttaaactgg aactggtgga aaaactgttt  420
gcggaagata ccgaagcgaa aaacccgttt agcacccaag ataccgatct ggatctggaa  480
atgctggcgc cgtatattcc gatggatgac gattttcagc tgcgcagctt tgatcagctg  540
agcccgctgg aaagcagcag tgcgagcccg gaaagcgcga gcccgcagag caccgtgacc  600
gtgtttcagt aa                                                      612

SEQ ID NO: 10          moltype = AA  length = 203
FEATURE                Location/Qualifiers
source                 1..203
                       mol_type = protein
                       organism = Homo sapiens
SEQUENCE: 10
APAAGDTIIS LDFGSNDTET DDQQLEEVPL YNDVMLPSPN EKLQNINLAM SPLPTAETPK  60
PLRSSADPAL NQEVALKLEP NPESLELSFT MPQIQDQTPS PSDGSTRQSS PEPNSPSEYC  120
FYVDSDMVNE FKLELVEKLF AEDTEAKNPF STQDTDLDLE MLAPYIPMDD DFQLRSFDQL  180
SPLESSSASP ESASPQSTVT VFQ                                          203

SEQ ID NO: 11          moltype = DNA  length = 170
FEATURE                Location/Qualifiers
source                 1..170
                       mol_type = other DNA
                       organism = synthetic construct
SEQUENCE: 11
ggccctacgt gctgtctcac acagcctgtc tgacggccct acgtgctgtc tcacacagcc  60
tgtctgacgg ccctacgtgc tgtctcacac agcctgtctg acggccctac gtgctgtctc  120
acacagcctg tctgacggcc ctacgtgctg tctcacacag cctgtctgac             170

SEQ ID NO: 12          moltype = DNA  length = 175
FEATURE                Location/Qualifiers
source                 1..175
```

```
                        mol_type = other DNA
                        organism = synthetic construct
SEQUENCE: 12
ccacagtgca tacgtgggct ccaacaggtc ctcttccaca gtgcatacgt gggctccaac  60
aggtcctctt ccacagtgca tacgtgggct ccaacaggtc ctcttccaca gtgcatacgt  120
gggctccaac aggtcctctt ccacagtgca tacgtgggct ccaacaggtc ctctt       175

SEQ ID NO: 13           moltype = DNA  length = 212
FEATURE                 Location/Qualifiers
source                  1..212
                        mol_type = genomic DNA
                        organism = Homo sapiens
SEQUENCE: 13
gggcagagcg cacatcgccc acagtccccg agaagttggg gggaggggtc ggcaattgaa  60
ccggtgccta gagaaggtgg cgcggggtaa actgggaaag tgatgtcgtg tactggctcc  120
gcctttttcc cgagggtggg ggagaaccgt atataagtgc agtagtcgcc gtgaacgttc  180
tttttcgcaa cgggtttgcc gccagaacac ag                                212

SEQ ID NO: 14           moltype = AA  length = 240
FEATURE                 Location/Qualifiers
source                  1..240
                        mol_type = protein
                        organism = synthetic construct
SEQUENCE: 14
EIVLTQSPGT LSLSPGERAT LSCRASQSVT SSYLAWYQQK PGQAPRLLIN VGSRRATGIP  60
DRFSGSGSGT DFTLTISRLE PEDFAVYYCQ QGIMLPPTFG QGTKVEIKGG GGSGGGGSGG  120
GGSEVQLLES GGGLVQPGGS LRLSCAASGF TFSSYAMSWV RQAPGKGLEW VSAIIGSGAS  180
TYYADSVKGR FTISRDNSKN TLYLQMNSLR AEDTAVYYCA KGWFGGFNYW GQGTLVTVSS  240

SEQ ID NO: 15           moltype = DNA  length = 30
FEATURE                 Location/Qualifiers
source                  1..30
                        mol_type = genomic DNA
                        organism = Homo sapiens
SEQUENCE: 15
gaagcagctg ctagaaaagc cgctgccaga                                   30

SEQ ID NO: 16           moltype = DNA  length = 162
FEATURE                 Location/Qualifiers
source                  1..162
                        mol_type = other DNA
                        organism = synthetic construct
SEQUENCE: 16
ttggacttag agatgttggc tccctatatc cccatggatg acgattttca gctgctggac  60
ctggaaatgc ttgcccccta catccctatg gatgacgact ttcagctgct ggacctggag  120
atgctcgccc cttacatccc gatggacgat gatttccaac tc                     162

SEQ ID NO: 17           moltype = AA  length = 54
FEATURE                 Location/Qualifiers
source                  1..54
                        mol_type = protein
                        organism = synthetic construct
SEQUENCE: 17
LDLEMLAPYI PMDDDFQLLD LEMLAPYIPM DDDFQLLDLE MLAPYIPMDD DFQL        54

SEQ ID NO: 18           moltype = DNA  length = 108
FEATURE                 Location/Qualifiers
source                  1..108
                        mol_type = genomic DNA
                        organism = Homo sapiens
SEQUENCE: 18
ttggacttag agatgttggc tccctatatc cccatggatg acgattttca gctgctggac  60
ctggaaatgc ttgcccccta catccctatg gatgacgact ttcagctg               108

SEQ ID NO: 19           moltype = AA  length = 36
FEATURE                 Location/Qualifiers
source                  1..36
                        mol_type = protein
                        organism = Homo sapiens
SEQUENCE: 19
LDLEMLAPYI PMDDDFQLLD LEMLAPYIPM DDDFQL                            36

SEQ ID NO: 20           moltype = DNA  length = 738
FEATURE                 Location/Qualifiers
source                  1..738
                        mol_type = other DNA
                        organism = synthetic construct
SEQUENCE: 20
gacatcgtga tgacccagtc ccccagctct ttaacagtca ccgccggaga gaaggtgacc  60
```

-continued

```
atgagctgca agtcctccca gtctttactg aacagcggca accagaagaa ctatttaaca  120
tggtaccagc agaagcccgg tcagcccccc aagttattaa tctactgggc cagcacaagg  180
gagagcggcg tgcccgatag attcaccggc agcggctccg gcaccgactt cacactgacc  240
atctccagcg tgcaagctga ggatttagcc gtgtactact gccagaacga ctacagctac  300
cccttcacct tcggcagcgg caccaagctg gagattaagg gcggcggcgg aagcggagga  360
ggaggctccg gaggaggagg atcccaagtt cagctgcagc agcccggtgc cgaactggtt  420
cgtcccggtg ccagcgtgaa gctgagctgc aaggcctccg gctacacctt caccagctac  480
tggatcaact gggtgaagca acgtcccggt caaggcttag aatggatcgg caacatctac  540
cccagcgact cctacaccaa ctacaaccag aagttcaagg acaaggccac cctcaccgtg  600
gataagagct ccagcacagc ctacatgcag ctgagcagcc ccacctccga ggatagcgcc  660
gtgtattact gtacaaggag ctggagaggc aacagctttg actactgggg ccaaggtaca  720
actttaaccg tgtccagc                                                 738

SEQ ID NO: 21          moltype = AA  length = 246
FEATURE                Location/Qualifiers
source                 1..246
                       mol_type = protein
                       organism = synthetic construct
SEQUENCE: 21
DIVMTQSPSS LTVTAGEKVT MSCKSSQSLL NSGNQKNYLT WYQQKPGQPP KLLIYWASTR  60
ESGVPDRFTG SGSGTDFTLT ISSVQAEDLA VYYCQNDYSY PFTFGSGTKL EIKGGGGSGG  120
GGSGGGGSQV QLQQPGAELV RPGASVKLSC KASGYTFTSY WINWVKQRPG QGLEWIGNIY  180
PSDSYTNYNQ KFKDKATLTV DKSSSTAYMQ LSSPTSEDSA VYYCTRSWRG NSFDYWGQGT  240
TLTVSS                                                              246

SEQ ID NO: 22          moltype = DNA  length = 726
FEATURE                Location/Qualifiers
source                 1..726
                       mol_type = other DNA
                       organism = synthetic construct
SEQUENCE: 22
gatgtggtga tgacgcagag cccgttaagc ctgccggtga ccccgggcga accggcgagc  60
attagctgcc gcagcagtca gagcctggtg catagcaacg cgaacaccta tctgcattgg  120
tatctgcaga aaccgggtca gagcccgcag ctgctgattt ataaagtgag caaccgcttt  180
agcggcgtgc cggatcgctt cagcggcagc ggtagcggca ccgattttac cctgaaaatt  240
agccgcgtgg aagcggaaga tgtgggcgtg tattattgca gtcagaacac ccatgtgccg  300
ccgacctttg gtcaaggcac gaaactggaa attaaaggcg gtggcggcag cggcggtggc  360
ggcagcggtg gcggtggcag tcaagtgcag ctggtgcaga gcggcgcgga agtgaaaaaa  420
ccgggcgcga gcgtgaaagt gagctgcaaa gcgagcggct atacctttac cgattatgaa  480
atgcattggg tgcgccaagc gccgggccaa ggcctggaat ggatgggcgc gctggatccg  540
aaaaccggcg ataccgcgta tagtcagaaa tttaaaggcc gcgtgaccct gaccgcggat  600
gaaagcacga gcaccgcgta tatggaactg agcagcctgc gcagcgaaga taccgcggtt  660
tattattgca cgcgctttta tagctatacc tattggggcc aaggcacgtt agtgaccgtg  720
agcagc                                                              726

SEQ ID NO: 23          moltype = AA  length = 242
FEATURE                Location/Qualifiers
source                 1..242
                       mol_type = protein
                       organism = synthetic construct
SEQUENCE: 23
DVVMTQSPLS LPVTPGEPAS ISCRSSQSLV HSNANTYLHW YLQKPGQSPQ LLIYKVSNRF  60
SGVPDRFSGS GSGTDFTLKI SRVEAEDVGV YYCSQNTHVP PTFGQGTKLE IKGGGGSGGG  120
GSGGGGSQVQ LVQSGAEVKK PGASVKVSCK ASGYTFTDYE MHWVRQAPGQ GLEWMGALDP  180
KTGDTAYSQK FKGRVTLTAD ESTSTAYMEL SSLRSEDTAV YYCTRFYSYT YWGQGTLVTV  240
SS                                                                  242

SEQ ID NO: 24          moltype = AA  length = 15
FEATURE                Location/Qualifiers
source                 1..15
                       mol_type = protein
                       organism = synthetic construct
SEQUENCE: 24
GGGGSGGGGS GGGGS                                                    15

SEQ ID NO: 25          moltype = AA  length = 241
FEATURE                Location/Qualifiers
source                 1..241
                       mol_type = protein
                       organism = synthetic construct
SEQUENCE: 25
EIVMTQSPAT LSVSPGERAT LSCRASQSVS RNLAWYQQKP GQAPRLLIYG ASTRATGIPA  60
RFSGSGSGTE FTLTIGSLQS EDFAVYYCQQ YKTWPRTFGQ GTNVEIKGGG GSGGGGSGGG  120
GSQVQLQQWG AGLLKPSETL SLTCAVFGGS FSGYYWSWIR QPPGKGLEWI GEINHRGNTN  180
DNPSLKSRVT ISVDTSKNQF ALKLSSVTAA DTAVYYCARE RGYTYGNFDH WGQGTLVTVS  240
S                                                                   241

SEQ ID NO: 26          moltype = DNA  length = 54
FEATURE                Location/Qualifiers
```

-continued

```
source                  1..54
                        mol_type = genomic DNA
                        organism = Homo sapiens
SEQUENCE: 26
ttggacttag agatgttggc tccctatatc cccatggatg acgattttca gctg       54

SEQ ID NO: 27           moltype = AA  length = 18
FEATURE                 Location/Qualifiers
source                  1..18
                        mol_type = protein
                        organism = Homo sapiens
SEQUENCE: 27
LDLEMLAPYI PMDDDFQL                                               18
```

ENHANCED CHIMERIC ANTIGEN RECEPTOR CELLS IN HYPOXIC TUMOR MICROENVIRONMENT

CROSS REFERENCE TO RELATED APPLICATIONS

This application claims the benefit of U.S. Provisional Patent Application 63/300,868, filed on Jan. 19, 2022, and U.S. Provisional Patent Application 63/351,200, filed on Jun. 10, 2022, which are hereby incorporated by reference in their entirety.

SEQUENCE LISTING INFORMATION

A computer-readable textfile, entitled "ST25 Finalized," created on or about Jan. 10, 2023, with a file size of about 30,821 bytes, contains the sequence listing for this application and is hereby incorporated by reference in its entirety.

BACKGROUND

Cancer involves abnormal cell growth with the potential to invade or spread to other parts of the body. Once cancer cells are exfoliated, they spread over the entire body via the blood and/or lymphatic systems and therefore become life-threatening. While T cell therapies have provided vigorous antitumor activities against blood tumors, they face challenges in treating solid tumors.

SUMMARY

Embodiments of the present disclosure relate to compositions and methods of enhancing lymphocytes' ability to treat cancer patients. Embodiments relate to a polynucleotide comprising a nucleic acid encoding a chimeric antigen receptor (CAR), a nucleic acid encoding an oxygen-dependent degradation (ODD) domain, and a nucleic acid encoding one or multiple sequences of hypoxia-response element (HRE).

This Summary is not intended to identify key features or essential features of the claimed subject matter, nor is it intended to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIG. 4 shows structures of hypo CLDN18.2 CARs and the killing ability of T cells expressing these hypo CLDN18.2 CARs and conventional CLDN18.2 CAR when co-cultured with substrate cells. "175" refers to CLDN 18.2 scFv. "LV" refers to lentiviral vector. "9×HRE" is shown in SEQ ID NO: 1 (HRE repeated 9×). "BBZ" or "bbz" refers 4-1BB and CD3 zeta. "ODD" refers to the full length oxygen dependent degradation domain (SEQ ID NO: 10). "MiniODD" refers to a portion of ODD (SEQ ID NO: 27) repeated 3×.

FIGS. 6A, 6B, and 6C show structures of hypo GPC3 CARs and cytokine release by CAR T cells expressing hypo GPC3 CARs and conventional GPC3 CAR when co-cultured with substrate cells. "GPC3" refers to GPC3 scFv. "LV" refers to lentiviral vector. "9×HRE" is shown in SEQ ID NO: 1 (HRE repeated 9×). "BBZ" or "bbz" refers 4-1BB and CD3 zeta. "ODD" refers to the full length oxygen dependent degradation domain (SEQ ID NO: 10). "MiniODD" refers to a portion of ODD (SEQ ID NO: 27) repeated 3×.

DETAILED DESCRIPTION

Figure 1:
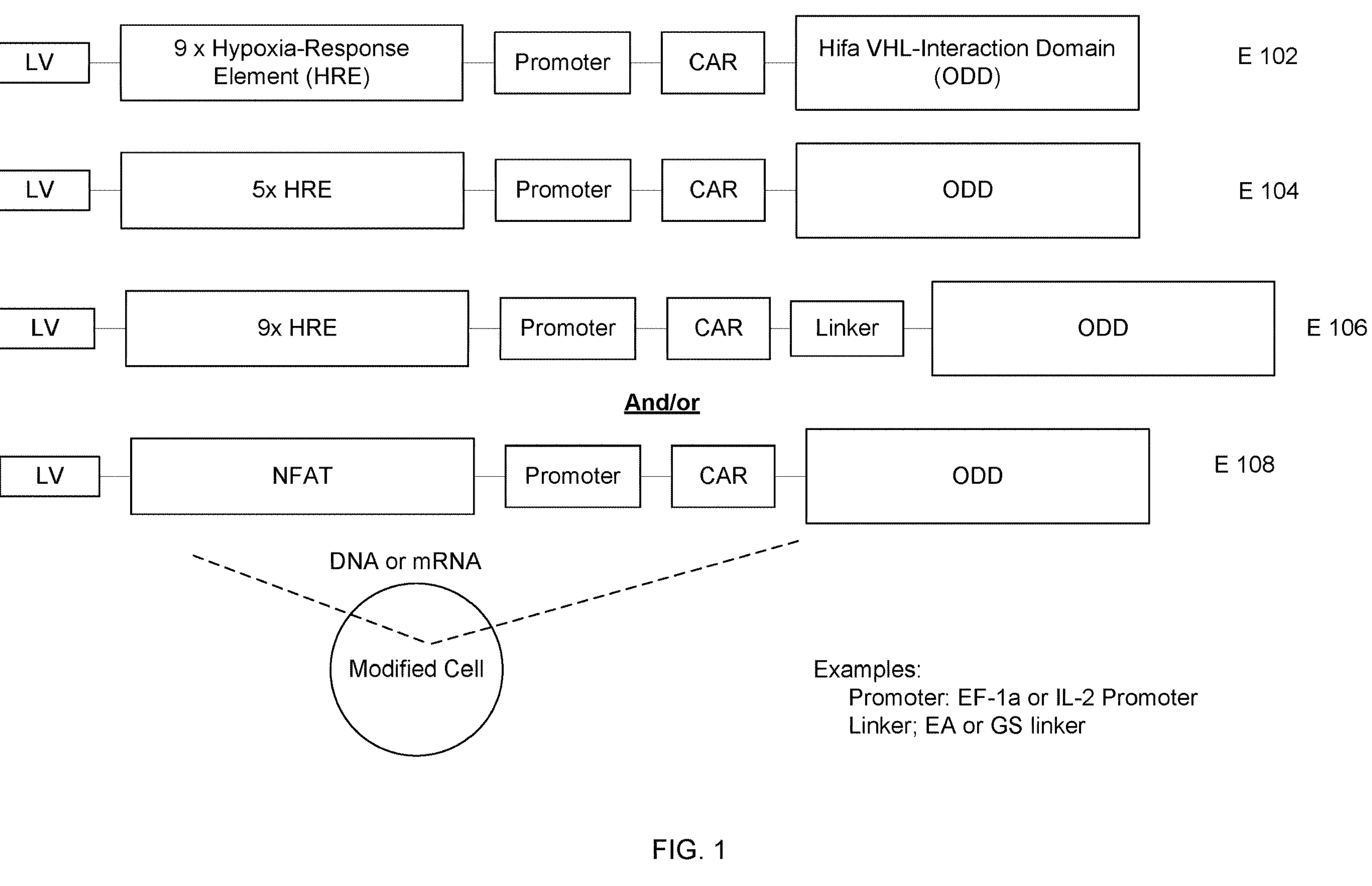
FIG. 1 is a schematic diagram of exemplary modified cells.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, and Fv, Fab, Fab' and F(ab')2 and fragments, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute the amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and A light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody, or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumor in the first place.

The term "autoantigen" or "self-antigen" refers to an antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject which is subsequently re-introduced into the same subject.

The term "allogeneic" is used to describe a graft derived from a different subject of the same species. As an example, a donor subject may be related or unrelated to the recipient subject, but the donor subject has immune system markers which are similar to the recipient subject.

The term "xenogeneic" is used to describe a graft derived from a subject of a different species. As an example, the donor subject is from a different species than a recipient subject and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Cancers that may be treated include tumors that are not vascularized, or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
|---|---|
| PRLR | Breast Cancer |
| CLCA1 | colorectal Cancer |
| MUC12 | colorectal Cancer |
| GUCY2C (GCC) | colorectal Cancer |
| GPR35 | colorectal Cancer |
| CR1L | Gastric Cancer |
| MUC 17 | Gastric Cancer |
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM 12 | Breast cancer, pancreatic cancer and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesothelioma |
| GPC3 | Lung squamous cell carcinoma |
| IL-13Rα2 (IL-13 receptor alpha 2) | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomas |
| EpCAM | Carcinomas |
| EGFRvIII | Glioma-Glioblastoma |
| EGFR | Glioma-NSCL cancer |
| tMUC 1 | Cholangiocarcinoma, Pancreatic cancer, |
| PSCA | pancreas, stomach, or prostate cancer |

The term "tumor associated antigens (TAAs)" as used herein refers to antigens selectively expressed or overexpressed by malignant cells in a tissue with a tumor as compared with a corresponding normal tissue. The tumor associated antigens include various groups such as tumor specific antigens, oncogetal antigens, oncogene products, organ lineage antigens, viral antigens, etc. For example, oncogene and suppressor gene products, such as nonmutated HER-2/neu and p53, are analogous to oncofetal antigens in that they can be overexpressed in tumors and may be expressed in some fetal tissues. Additional examples of TAAs include Fibroblast activation protein-α (FAP), HER2, MART-1, MUC1, tyrosinase, MAGE, mammaglobin-A, and NY-ESO-1.

For example, FAP is a type II integral serine protease that is specifically expressed by activated fibroblasts. Cancer-associated fibroblasts (CAFs) in the tumor stroma have an abundant and stable expression of FAP, which plays an important role in promoting tumor growth, invasion, metastasis, and immunosuppression. For example, in females with a high incidence of breast cancer, CAFs account for 50-70% of the cells in the tumor's microenvironment. CAF overexpression of FAP promotes tumor development and metastasis by influencing extracellular matrix remodeling, intracellular signaling, angiogenesis, epithelial-to-mesenchymal transition, and immunosuppression.

The term "tumor specific antigens (TSAs)" as used herein refers to antigens that are uniquely expressed in tumors, such as point-mutated ras oncogenes, p53 mutations, anti-idiotype antibodies (Abs), and products of ribonucleic acid (RNA) splice variants, and gene translocations. Another example of TSA is tumor form of human MUC1 (tMUC1).

For example, MUC1 is one of the epithelial mucin family of molecules. MUC1 is a transmembrane mucin glycoprotein that is normally expressed on all glandular epithelial cells of the major organs. In normal cells, MUC1 is only expressed on the apical surface and is heavily glycosylated with its core proteins sequestered by the carbohydrates. As cells transform to a malignant phenotype, expression of MUC1 increases several folds, and the expression is no longer restricted to the apical surface, but it is found all around the cell surface and in the cytoplasm. In addition, the glycosylation of tumor associated MUC1 (tMUC1) is aberrant, with greater exposure of the peptide core than is found on MUC1 expressed in normal tissues.

The term "organ lineage antigen (OLA)" as used herein refers to an antigen expressed in a tumor of a given type and the normal organ from which the tumor is derived. Examples of organ lineage antigen include prostate-specific antigen (PSA) and the melanocyte antigens, such as CD19, BCMA, CD20, CD22, GCC, PAP, MSLN, and ALPP. Organ lineage antigens can serve as targets for immunotherapy if the normal organ in which they are expressed is not essential, such as the prostate, breast, or melanocyte. As used herein, an organ refers to an integrated group of cells with a common structure, an intercellular material, and/or a function.

For example, guanylyl cyclase 2C (GUCY2C or GCC) is principally expressed in intestinal epithelial cells. GUCY2C is the receptor for diarrheagenic bacterial enterotoxins and the gut paracrine hormones, guanylin, and uroguanylin. These ligands regulate water and electrolyte transport in the intestinal and renal epithelia and are ultimately responsible for acute secretory diarrhea.

Throughout this specification, unless the context requires otherwise, the words "comprise," "includes" and "including" will be understood to imply the inclusion of a stated step or element (ingredient or component) or group of steps or elements (ingredients or components) but not the exclusion of any other step or element or group of steps or elements.

The phrase "consisting of" is meant to include, and is limited to, whatever follows the phrase "consisting of." Thus, the phrase "consisting of" indicates that the listed elements or steps are required or mandatory and that no other elements may be present.

The phrase "consisting essentially of" is meant to include any element listed after the phrase and can include other elements or steps that do not interfere with or contribute to the activity or action specified in the disclosure for the listed elements or steps. Thus, the phrase "consisting essentially of" indicates that the listed elements or steps are required or mandatory, but that other elements or steps are optional and may or may not be present depending upon whether or not they affect the activity or action of the listed elements or steps. In embodiments, those elements or steps that do not affect an embodiment are those elements or steps that do not alter the embodiment's ability in a statistically significant manner to perform a function in vitro or in vivo, such as killing cancer cells in vitro or in vivo.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand" refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules.

The terms "co-stimulatory signaling region", "co-stimulatory domain", and "co-stimulation domain" are used interchangeably to refer to one or more additional stimulatory domain in addition to a stimulatory or signaling domain such as CD3 zeta. The terms "stimulatory" or "signaling" domain (or region) are also used interchangeably, when referring, for example, to CD3 zeta. In embodiments, the co-stimulatory signaling domain and the signaling domain can be on the same molecule or different molecules in the same cell.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for the synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses (AAV)) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially free from components that normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables integration of the genetic information into the host chromosome resulting in stably transduced genetic information. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein, and refer to any animal, such as a mammal, for example, a human or any living organism amenable to the methods described herein.

In embodiments, the patient, subject, or individual is a human or mammal. In embodiments, the term "subject" is intended to include living organisms in which an immune response can be elicited (e.g., mammals). Examples of subjects include humans, and animals such as dogs, cats, mice, rats, and transgenic species thereof.

A subject in need of treatment or in need thereof includes a subject having a disease, condition, or disorder that needs to be treated. A subject in need thereof also includes a subject that needs treatment for prevention of a disease, condition, or disorder. Accordingly, the subject can also be in need of prevention of a disease condition or disorder. In embodiments, the disease is cancer.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In embodiments, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control (regulatory) sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

"NFAT promoter" refers to one or more NFAT binding sites or motifs linked to a minimal promoter of any gene expressed by T cells. In embodiments, the minimal promoter of a gene expressed by T cells is a minimal human IL-12 promoter. Nuclear factor of activated T cells (NFAT) are transcription factors. Examples of NFAT transcription factors include NFAT1, NFAT2, NFAT3, NFAT4, and NFAT5. These transcription factors bind NFAT binding sites or motifs in the NFAT promoter. The NFAT promoter (or a functional portion or functional variant thereof) can comprise any number of binding motifs, e.g., at least two, at least three, at least four, at least five, or at least six, at least seven, at least eight, at least nine, at least ten, at least eleven, or up to twelve binding motifs. In embodiments, the NFAT promoter comprises six NFAT binding motifs.

The NFAT promoter (or a functional portion or functional variant thereof) is operatively associated with the nucleotide sequence encoding IL-12 (or a functional portion or functional variant thereof). "Operatively associated with" means that the nucleotide sequence encoding IL-12 (or a functional portion or functional variant thereof) is transcribed into IL-12 mRNA when the NFAT protein binds to the NFAT promoter sequence (or a functional portion or functional variant thereof). Without being bound to a particular theory, it is believed that NFAT is regulated by a calcium signaling pathway. In particular, it is believed that TCR stimulation (by, e.g., an antigen) and/or stimulation of the calcium signaling pathway of the cell (by, e.g., PMA/lonomycin) increases intracellular calcium concentration and activates calcium channels. It is believed that the NFAT protein is then dephosporylated by calmoduin and translocates to the nucleus where it binds the NFAT promoter sequence (or a functional portion or functional variant thereof) and activates downstream gene expression. By providing an NFAT promoter (or a functional portion or functional variant thereof) that is operatively associated with the nucleotide sequence encoding IL-12 (or a functional portion or functional variant thereof), the nucleic acids described herein advantageously make it possible to express IL-12 (or a functional portion or functional variant thereof) only when the host cell including the nucleic acid is stimulated by, e.g., PMA/lonomycin and/or an antigen. More information can be found at U.S. Pat. No. 8,556,882, which is incorporated by the reference.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Further, a Zinc finger binding domain may be fused a DNA-cleavage domain to form a Zinc finger nuclease (ZFN) targeting a specific desired DNA sequence. For example, a pair of ZFNs (e.g., a ZFN-left arm and a ZFN-right arm) may be engineered to target and cause modifications of specific desired DNA sequences (e.g., TRAC genes).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In embodiments, fusion polypeptides are used for targeted double-stranded DNA cleavage.

A "target site" or "target sequence" is a nucleic acid sequence that defines a portion of a nucleic acid to which a binding molecule will bind, provided sufficient conditions for binding exist. For example, the sequence 5' GAATTC 3' is a target site for the Eco RI restriction endonuclease.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage, and polypeptide ligation can also be involved in the expression of the protein in a cell. Methods for polynucleotide and polypeptide delivery to cells are presented elsewhere in this disclosure.

"Modulation" of gene expression refers to a change in the activity of a gene. Modulation of expression can include but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures. CD3 zeta is not the only suitable primary signaling domain for a CAR construct with respect to the primary response. For example, back in 1993, both CD3 zeta and FcRy were shown as functional primary signaling domains of CAR molecules. Eshhar et al., "Specific activation and targeting of cytotoxic lymphocytes through chimeric single chains consisting of antibody-binding domains and the gamma or zeta subunits of the immunoglobulin and T cell receptors" PNAS, 1993 Jan. 15; 90(2):720-4, showed that two CAR constructs in which an scFv was fused to "either the FcR gamma chain or the CD3 complex chain" triggered T cell activation and target cell. Notably, as demonstrated in Eshhar et al., CAR constructs containing only the primary signaling domain CD3 zeta or FcR gamma are functional without the co-presence of co-stimulatory domains. Additional non-CD3 zeta based CAR constructs have been developed over the years. For example, Wang et al. ("A Chimeric Antigen Receptor (CARs) Based Upon a Killer Immunoglobulin-Like Receptor (KIR) Triggers Robust Cytotoxic Activity in Solid Tumors" Molecular Therapy, vol. 22, no. Suppl. 1, May 2014, page S57) tested a CAR molecule in which an scFv was fused to "the transmembrane and cytoplasmic domain of" a killer immunoglobulin-like receptor (KIR). Wang et al. reported that, "a KIR-based CAR targeting mesothelin (SS 1-KIR) triggers antigen-specific cytotoxic activity and cytokine production that is comparable to CD3~-based CARs." A second publication from the same group, Wang et al. ("Generation of Potent T-cell Immunotherapy for Cancer Using DAP12-Based, Multichain, Chimeric Immunoreceptors" Cancer Immunol Res. 2015 July; 3(7):815-26) showed that a CAR molecule in which "a single-chain variable fragment for antigen recognition was fused to the transmembrane and cytoplasmic domains of KIR2DS2, a stimulatory killer immunoglobulin-like receptor (KIR)" functioned both in vitro and in vivo "when introduced into human T cells with DAP12, an immunotyrosine-based activation motifs-containing adaptor."

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. The cell can be an in vitro cell or a in vivo cell in a subject. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate transfer of nucleic acid into cells, such as, for example, polylysine compounds, liposomes, and the like. Examples of viral vectors include, adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

In embodiments, a polynucleotide encoding the antigen binding molecule and/or therapeutic agent(s) can be used to implement techniques described herein. The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide; and administering an amount of the viral particle to the subject such that the polynucleotide is expressed in the subject. In embodiments, the AAV preparation may include AAV vector particles, empty capsids and host cell impurities, thereby providing an AAV product substantially free of AAV empty capsids. More information of the administration and preparation of the viral particle may be found at the U.S. Pat. No. 9,840,719 and Milani et al., Sci. Transl. Med. 11, eaav7325 (2019) 22 May 2019, which are incorporated herein by reference. In embodiments, the polynucleotide may integrate into the genome of the modified cell and the progeny of the modified cell will also express the polynucleotide, resulting in a stably transfected modified cell. In embodiments, the modified cell expresses the polynucleotide encoding the CAR but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The T cell response in a subject refers to cell-mediated immunity associated with a helper, killer, regulatory, and other types of T cells. For example, T cell response may include activities such as assistance to other white blood cells in immunologic processes and identifying and destroying virus-infected cells and tumor cells. T cell response in the subject may be measured via various indicators such as the number of virus-infected cells and/or tumor cells that T cells kill, an amount of cytokines that T cells release, for example, in co-culturing with virus-infected cells and/or tumor cells, a level of proliferation of T cells in the subject, a phenotype change of T cells (e.g., changes to memory T cells), and the longevity or lifespan of T cells in the subject.

In embodiments, in vitro killing assay may be performed by measuring the killing efficacy of CAR T cells by co-culturing CAR T cells with antigen-positive cells. CAR T cells may be considered to have killing effect on the corresponding antigen-positive cells by showing a decrease in the number of corresponding antigen-positive cells co-cultured with CAR T cells and an increase in the release of cytokines such as IFN-γ, TNF-α, and the like, as compared to control cells that do not express the corresponding antigen. Further, in vivo antitumor activity of the CAR T cells may be tested. For example, xenograft models can be established using the antigens described herein in immunodeficient mice. Heterotransplantation of human cancer cells or tumor biopsies into immunodeficient rodents (xenograft models) has, for the past two decades, constituted the major preclinical screen for the development of novel cancer therapeutics (Song et al., Cancer Res. PMC 2014 Aug. 21, and Morton et al., Nature Protocols, 2, -247-250 (2007)). To evaluate the anti-tumor activity of CAR T cells in vivo, immunodeficient mice bearing tumor xenografts were evaluated for CAR T cell anti-tumor activity, for example, a decrease in mouse tumors and/or mouse blood cytokines, such as IFN-γ, TNF-α, and the like.

The term "chimeric antigen receptor" or alternatively a "CAR" refers to a recombinant polypeptide construct comprising at least an extracellular antigen binding domain, a transmembrane domain, and an intracellular signaling domain (e.g., cytoplasmic domain). In embodiments, the domains in the CAR polypeptide are on the same polypeptide chain (e.g., comprising a chimeric fusion protein). In embodiments, the domains of the CAR polypeptide are not on the same molecule, e.g. not contiguous with each other, or are on different polypeptide chains.

In embodiments, the intracellular signaling domain may include a functional signaling domain derived from a stimulatory molecule and/or a co-stimulatory molecule as described herein. In embodiments, the intracellular signaling domain includes a functional signaling domain derived from a primary signaling domain (e.g., a primary signaling domain of CD3-zeta). In embodiments, the intracellular signaling domain further includes one or more functional signaling domains derived from at least one co-stimulatory molecule. The co-stimulatory signaling region refers to a portion of the CAR including the intracellular domain of a co-stimulatory molecule. Co-stimulatory molecules can include cell surface molecules for inducing an efficient response from the lymphocytes (in response to an antigen).

Between the extracellular domain and the transmembrane domain of the CAR, there can be incorporated a spacer domain. As used herein, the term "spacer domain" generally means any oligo- or polypeptide that functions to link the transmembrane domain to the extracellular domain and/or the cytoplasmic domain in the polypeptide chain. A spacer domain may include up to 300 amino acids, 10 to 100 amino acids, or 25 to 50 amino acids.

The extracellular domain of a CAR may include an antigen binding domain (e.g., a scFv, a single domain antibody, or TCR, such as a TCR alpha binding domain or a TCR beta binding domain), that targets a specific tumor marker (e.g., a tumor antigen). Tumor antigens are proteins that are produced by tumor cells that elicit an immune response, particularly T cell mediated immune responses. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. For example, when the antigen that the CAR binds is CD19, the CAR thereof is referred to as CD19 CAR (19CAR, CD19CAR, CD19 CAR, or CD19-CAR), which is a CAR molecule that includes an antigen binding domain that binds CD19.

In embodiments, the extracellular ligand-binding domain comprises a scFv comprising the light chain variable (VL) region and the heavy chain variable (VH) region of a target antigen-specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)3 (SEQ ID: 24), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides comprising about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

In embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor a 2, IL-11 receptor a, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by a tumor. In embodiments, the binding element of the CAR includes any antigen binding moiety that when bound to its cognate antigen, affects a tumor cell such that the tumor cell fails to grow, decrease in size, or dies.

The CAR can be a bispecific CAR. For example, the two antigen binding domains are on the same CAR (a bispecific CAR or tandem CAR (tanCAR)), on different CAR molecules, or on a CAR and T cell receptor (TCR). A single CAR can include two different antigen binding domains, or the two different antigen binding domains are each on a separate CAR. The CAR can have more than two antigen binding domains, for example, a multispecific CAR. The antigen binding domains of the multispecific CAR can be on the same CAR or on separate CAR, such as one antigen binding domain on each CAR.

In embodiments, the intracellular domain of the CAR comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

In embodiments, the intracellular domain comprises a CD3 zeta signaling domain. Embodiments relate to a vector comprising the isolated nucleic acid sequence described herein. Embodiments relate to an isolated cell comprising the isolated nucleic acid sequence described herein.

The cells, including CAR cells and modified cells, described herein can be derived from a stem cell. The stem cells may be adult stem cells, embryonic stem cells, or non-human stem cells, cord blood stem cells, progenitor cells, bone marrow stem cells, induced pluripotent stem cells, totipotent stem cells, or hematopoietic stem cells. The cells can also be a dendritic cell, a NK-cell, a B-cell, or a T cell selected from the group consisting of inflammatory T lymphocytes, cytotoxic T lymphocytes, regulatory T lymphocytes, and helper T lymphocytes. In embodiments, the cells can be derived from the group consisting of CD4+ T-lymphocytes and CD8+ T-lymphocytes. Prior to expansion and genetic modification of the cells described herein, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art, can be used. In embodiments, the cells may be derived from a healthy donor, from a patient diagnosed with cancer, or from a patient diagnosed with an infection. In embodiments, the cells are part of a mixed population of cells which present different phenotypic characteristics.

A population of cells refers to a group of two or more cells. The cells of the population could be the same, such that the population is a homogenous population of cells. The cells of the population could be different, such that the population is a mixed population or a heterogeneous population of cells. For example, a mixed population of cells could include modified cells comprising a first CAR and cells comprising a second CAR, wherein the first CAR and the second CAR bind different antigens.

The term "stem cell" refers to any type of cell which has the capacity for self-renewal and the ability to differentiate into other kind(s) of cell. For example, a stem cell gives rise either to two daughter stem cells (as occurs in vitro with embryonic stem cells in culture) or to one stem cell and a cell that undergoes differentiation (as occurs e.g. in hematopoietic stem cells, which give rise to blood cells). Different categories of stem cells may be distinguished on the basis of their origin and/or on the extent of their capacity for differentiation into other types of cell. Stem cells can include embryonic stem (ES) cells (i.e., pluripotent stem cells), somatic stem cells, induced pluripotent stem cells, and any other types of stem cells.

Pluripotent embryonic stem cells can be found in the inner cell mass of a blastocyst and have high innate capacity for differentiation. For example, pluripotent embryonic stem cells have the potential to form any type of cell in the body. When grown in vitro for long periods of time, ES cells maintain pluripotency, and progeny cells retain the potential for multilineage differentiation.

Somatic stem cells can include fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited number of different types of cells and have been described as multipotent. "Tissue-specific" stem cells normally give rise to only one type of cell. For example, embryonic stem cells can differentiate into blood stem cells (e.g., Hematopoietic stem cells (HSCs)), which can further differentiate into various blood cells (e.g., red blood cells, platelets, white blood cells, etc.).

Induced pluripotent stem cells (iPS cells or iPSCs) can include a type of pluripotent stem cell artificially derived from a non-pluripotent cell (e.g., an adult somatic cell) by inducing expression of specific genes. Induced pluripotent stem cells are similar to naturally occurring pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be isolated from adult stomach, liver, skin cells, and blood cells.

In embodiments, the CAR cells, the modified cell, or the cell is a T cell, a NK cell, a macrophage or a dendritic cell. For example, the CAR cells, the modified cell, or the cell is a T cell.

T cells, or T lymphocytes, are a type of white blood cell of the immune system. There are various types of T cells including T helper (TH) cells, cytotoxic T (TC) cells (T killer cells, killer T cells), natural killer T (NKT) cells, memory T (Tm) cells, regulatory T (Treg) cells, and gamma delta T (γδ T) cells.

T helper (TH) cells assist other lymphocytes, for example, activating cytotoxic T cells and macrophages and maturation of B cells into plasma cells and memory B cells. These T helper cells express CD4 glycoprotein on their surface and are also known as CD4+ T cells. Once activated, these T cells divide rapidly and secrete cytokines.

Cytotoxic T (TC) cells destroy virus-infected cells and tumor cells and are also involved in transplant rejection. They express CD8 protein on their surface. Cytotoxic T cell release cytokines.

Natural Killer T (NKT) cells are different from natural killer cells. NKT cells recognize glycolipid antigens presented by CD1d. Once activated, NKT cells produce cytokine and release cell killing molecules.

Memory T (Tm) cells are long-lived and can expand to large number of effector T cells upon re-exposure to their cognate antigen. Tm cells provide the immune system with memory against previously encountered pathogens. There are various subtypes of Tm cells including central memory T (TCM) cells, effector memory T (TEM) cells, tissue resident memory T (TRM) cells, and virtual memory T cells. Tm cells are either CD4+ or CD8+ and usually CD45RO.

Regulatory T (Treg) cells shut down T cell mediated immunity at the end of an immune reaction and suppress autoreactive T cells that escaped the process of negative selection in the thymus. Subsets of Treg cells include thymic Treg and peripherally derived Treg. Both subsets of Treg require the expression of the transcription factor FOXP3.

Gamma delta T (γδ T) cells are a subset of T cells that possess a γδ T cell receptor (TCR) on the cell surface, as most T cells express the αβ TCR chains. γδ T cells are less common in human and mice and are mainly found in the gut mucosa, skin, lung, and uterus. They are involved in the initiation and propagation of immune responses.

In embodiments, the antigen binding molecule is a T Cell Receptor (TCR). In embodiments, the TCR is modified TCR. In embodiments, the TCR is derived from spontaneously occurring tumor-specific T cells in patients. In embodiments, the TCR binds a tumor antigen. In embodiments, the tumor antigen comprises CEA, gp100, MART-1, p53, MAGE-A3, or NY-ESO-1. In embodiments, the TCR comprises TCRγ and TCRδ chains or TCRα and TCRβ chains.

In embodiments, a T cell clone that expresses a TCR with high affinity for the target antigen may be isolated. In embodiments, tumor-infiltrating lymphocytes (TILs) or peripheral blood mononuclear cells (PBMCs) may be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ chains are identified and isolated by molecular cloning. For example, for TCRα and TCRδ chains, the TCRα and TCRδ gene sequences are then used to generate an expression construct that ideally promotes stable, high-level expression of both TCR chains in human T cells. The transduction vehicle (e.g., a gammaretrovirus or lentivirus) may be then generated and tested for functionality (antigen specificity and functional avidity) and used to produce a clinical lot of the vector. An aliquot of the final product is then used to transduce the target T cell population (generally purified from patient PBMCs), which is expanded before infusion into the subject.

In embodiments, the APCs include dendritic cells, macrophages, Langerhans cells and B cells, or T cells.

In embodiments, the binding element of the CAR may include any antigen binding moiety that when bound to its cognate antigen, affects a tumor cell for example, it kills the tumor cell, inhibits the growth of the tumor cell, or promotes death of the tumor cell.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The embodiments of the present disclosure further relate to vectors in which a nucleic acid described herein is inserted. Vectors can be derived from retroviruses such as the lentivirus that are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Viruses can be used to deliver nucleic acids into a cell in vitro and in vivo (in a subject). Examples of viruses useful for delivery of nucleic acids into cells include retrovirus, adenovirus, herpes simplex virus, vaccinia virus, and adeno-associated virus.

There also exist non-viral methods for deliverying nucleic acids into a cell, for example, electroporation, gene gun, sonoporation, magnetofection, and the use of oligonucleotides, lipoplexes, dendrimers, and inorganic nanoparticles.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration into eukaryotes. Typical cloning vectors contain transcription and translation terminators, initiation sequences, and promoters useful for regulation of the expression of the desired nucleic acid sequence.

Additional information related to expression of synthetic nucleic acids encoding CARs and gene transfer into mammalian cells is provided in U.S. Pat. No. 8,906,682, incorporated by reference in its entirety.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", "therapeutic amount", or "effective amount" is indicated, the precise amount of the compositions of the present disclosure to be administered can be determined by a physician with consideration of individual differences in age, weight, tumor size, extent of infection or metastasis, and condition of the patient (subject). It can be stated that a pharmaceutical composition comprising the T cells described herein may be administered at a dosage of 104 to 109 cells/kg body weight, preferably 105 to 106 cells/kg body weight, including all integer values within those ranges. T cell compositions can also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art by monitoring the patient for signs of disease and adjusting the treatment accordingly. In embodiments, activated T cells are administered to a subject and then subsequently blood is redrawn (or have apheresis performed). T cells are collected, expanded, and reinfused into the subject. This process can be carried out multiple times every few weeks. In embodiments, T cells can be activated from blood draws of from 10 cc to 400 cc. In embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, certain populations of T cells can be selected.

The administration of the pharmaceutical compositions described herein can be carried out in any convenient manner, including by aerosol inhalation, injection, ingestion, transfusion, implantation or transplantation. The pharmaceutical compositions described herein can be administered to a patient subcutaneously, intradermally, intratumorally, intranodally, intramedullary, intramuscularly, intravenously (i. v.), or intraperitoneally. In embodiments, the T cell compositions of the present disclosure are administered to a patient by intradermal or subcutaneous injection. In embodiments, the T cell compositions of the present disclosure are administered by i.v. injection. The compositions of T cells may be injected directly into a tumor, lymph node, or site of infection. In embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In embodiments, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In embodiments, the cell compositions of the present disclosure are administered following B-cell ablative therapy such as agents that react with CD20, e.g., Rituxan®. For example, subjects may undergo standard treatment with high dose chemotherapy followed by peripheral blood stem cell transplantation. In embodiments, following the transplant, subjects receive an infusion of the expanded immune cells of the present disclosure. In embodiments, expanded cells are administered before or following surgery.

The dosage of the above treatments to be administered to a patient will vary with the precise nature of the condition being treated and the recipient of the treatment. The scaling of dosages for human administration can be performed according to art-accepted practices by a physician depending on various factors.

Additional information on the methods of cancer treatment using engineered or modified T cells is provided in U.S. Pat. No. 8,906,682, incorporated by reference in its entirety.

In embodiments, the population of cells described herein is used in autologous CAR T cell therapy. In embodiments, the CAR T cell therapy is allogenic CAR T cell therapy, TCR T cell therapy, and NK cell therapy.

Embodiments relate to an in vitro method for preparing modified cells. The method may include obtaining a sample of cells from the subject. For example, the sample may include T cells or T cell progenitors. The method may further include transfecting the cells with a DNA encoding at least a CAR, culturing the population of CAR cells ex vivo in a medium that selectively enhances proliferation of CAR-expressing T cells.

In embodiments, the sample is a cryopreserved sample. In embodiments, the sample of cells is from umbilical cord blood or a peripheral blood sample from the subject. In embodiments, the sample of cells is obtained by apheresis or venipuncture. In embodiments, the sample of cells is a subpopulation of T cells.

As used herein, the term "gene fusion" refers to the fusion of at least a portion of a gene to at least a portion of an additional gene. The gene fusion need not include entire genes or exons of genes. In some instances, gene fusion is associated with alternations in cancer. A gene fusion product refers to a chimeric genomic DNA, a chimeric messenger RNA, a truncated protein or a chimeric protein resulting from a gene fusion. The gene fusion product may be detected by various methods described in U.S. Pat. No. 9,938,582, which is incorporated as a reference herein. A "gene fusion antigen" refers to a truncated protein or a chimeric protein that results from a gene fusion. In embodiments, an epitope of a gene fusion antigen may include a part of the gene fusion antigen or an immunogenic part of another antigen caused by the gene fusion. In embodiments, the gene fusion antigen interacts with, or is part of, cell membranes.

In embodiments, detection of mRNA and protein expression levels of the target molecules (e.g., CARs and cytokines) in human cells may be performed using experimental methods such as qPCR and FACS. Further, target molecules specifically expressed in the corresponding tumor cells with very low expression or undetectable expression in normal tissue cells may be identified.

In embodiments, In Vitro Killer Assay as well as killing experiment of CAR T Cells Co-Cultured with Antigen-Positive Cells can be performed. CAR T cells can exhibit a killing effect on the corresponding antigen-positive cells, a decrease in the number of corresponding antigen-positive cells co-cultured with CAR T cells, and an increase in the release of IFN-γ, TNF-α, etc. as compared to control cells that did not express the corresponding antigen.

In embodiments, In Vivo Killer Assay can be performed. For example, mice may be transplanted with corresponding antigen tumor cells, and tumorigenic, transfusion of CAR T cells, and a decrease in mouse tumors and mouse blood IFN-γ, TNF-α, and other signals can be defected.

Embodiments relate to a method of eliciting and/or enhancing T cell response in a subject having a solid tumor or treating a solid tumor in the subject, the method comprising administering an effective amount of T cells comprising the CAR described herein. In embodiments, the intracellular domain of the CAR comprises a co-stimulatory signaling region that comprises an intracellular domain of a co-stimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the intracellular domain comprises a CD3 zeta signaling domain.

Embodiments relate to a vector comprising the isolated nucleic acid described herein.

Embodiments relate to an isolated cell comprising the isolated nucleic acid sequence described herein. Embodiments relate to a composition comprising a population of T cells comprising the CAR described herein. Embodiments relate to a CAR encoded by the isolated nucleic acid sequence described herein. Embodiments relate to a method of eliciting and/or enhancing T cell response in a subject or treating a tumor of the subject, the method comprising: administering an effective amount of T cell comprising the CAR described herein.

In embodiments, the CAR molecules described herein comprise one or more complementarity-determining regions (CDRs) for binding an antigen of interest. CDRs are part of the variable domains in immunoglobulins and T cell receptors for binding a specific antigen. There are three CDRs for each variable domain. Since there is a variable heavy domain and a variable light domain, there are six CDRs for binding an antigen. Further since an antibody has two heavy chains and two light chains, an antibody can have twelve CDRs altogether for binding antigens.

In embodiments, the modified cells described herein includes a CAR molecule comprising at least two different antigen binding domains. The CAR molecule can be a bispecific CAR molecule. For example, the two antigen binding domains can be on the same CAR molecule, on different CAR molecules, or on a CAR molecule and T cell receptor (TCR). A single CAR can include at least two different antigen binding domains, or the two different antigen binding domains are each on a separate CAR molecule. The at least two different antigen binding domains can be on the same CAR molecule or different CAR molecules, but in the same modified cell. Moreover, the at least two different antigen binding domains can be on a CAR molecule and a T cell receptor in the same modified cell. In embodiments, the bispecific CAR molecule can include a binding domain binding an antigen of WBC (e.g., CD19) and a binding domain binding a solid tumor antigen. In embodiments, the bispecific CAR molecule may include two binding domains binding two different solid tumor antigens.

In embodiments, the at least two different antigen binding domains are on different CAR molecules which are expressed by different modified cells. Further, the one or more different antigen binding domains are on a CAR molecule and a T cell receptor, which are expressed by different modified cells.

While CAR T cell therapy provides vigorous antitumor activities against blood tumors, CAR T therapy alone, at least for certain solid tumor types, may not be enough to overcome the tumor microenvironment, inhibit tumor growth, and eventually treat cancer patients. Therapeutic agents such as cytokine may enhance cell therapy when immune cells are modified to express a therapeutic agent in the body of patients. However, the expression of therapeutic agents must be regulated to avoid potential toxicity caused by the therapeutic agents.

The present disclosure provides compositions and methods to treat cancer patients using modified cells expressing one or more therapeutic agents with engineered safety. In many cases, multiple safety controls may be needed. For example, NFAT driven cytokines such as IL12 have been used to safely drive IL12 to be expressed and secreted by T cells. In a scenario such as CoupledCAR®, solid tumor CAR T cells may be activated without contacting their antigens. In another scenario, normal tissue can express the antigen that CAR T cells bind. In these instances, the activated T cells can express and release IL12 until they are exhausted, increasing the risk of toxicity caused by IL12. Having a second safety switch can avoid this risk. In embodiments, additionally engineered safety control switch can enhance T cells' functionalities (e.g., expressing IL12) when the T cells enter the tumor microenvironment.

The present disclosure provides compositions and methods to treat cancer patients using modified cells expressing one or more therapeutic agents with engineered with one or more safety control switches. In many cases, multiple safety control switches may be needed. For example, HRE driven CAR has been used to safely control the expression of the CAR by T or NK cells.

The tumor microenvironment (TME) includes tumor cells, vasculature, extracellular matrix (ECM), stromal, and immune cells. The ECM includes numerous molecules (ECM molecules) classified traditionally into collagens, elastin, and microfibrillar proteins, proteoglycans including hyaluronan, and noncollagenous glycoproteins. Like the other components of the TME, the ECM of tumors differs significantly from that in normal tissues or organs. For example, the ECM of tumors influences malignancy and growth of the tumor as well as helps tumor cells resist therapies. A summary of the ECM can be found at Järveläinen H, Sainio A, Koulu M, Wight T N, Penttinen R. ECM molecules: potential targets in pharmacotherapy. Pharmacol Rev. 2009; 61(2):198-223. doi:10.1124/pr.109.001289, which is incorporated herein by reference in its entirety. In embodiments, examples of ECM molecules include Collagen I, Collagen III, Collagen VI, Collagen IV, and Fibronectin. In embodiments, the agent targeting the ECM refers to an agent that degrades and/or causes or increases the degradation of one or more ECM molecules. In embodiments, the agent targeting the ECM includes an agent targeting the synthesis of the ECM, including cytokine inhibitors and cytokines. Examples of the agent targeting the synthesis of the ECM include antibodies to TGF-β1, antibodies to TGF-β2, TGF-β1 signaling inhibitors and TGF-β receptor I kinase inhibitors, and antibodies to CTGF, recombinant TGF-β3, and recombinant interleukin-10. In embodiments, the agent targeting the ECM includes an agent targeting the degradation of the ECM. Examples of agents targeting the ECM's degradation include MMP inhibitors, collagenase, MMP-14 inhibitors, broad-spectrum MMP inhibitors, selective cathepsin K inhibitors, heparanase activity inhibitors, and/or collagenase stimulators. In embodiments, the agent targeting the ECM includes an agent targeting the signaling of the ECM. Examples of agents targeting the signaling of the ECM include antibodies to αv/β3 integrin, antibodies to α4/β7 integrin, and/or antibodies to α5/β1 integrin.

Embodiments of the present disclosure relate to compositions and methods of enhancing lymphocytes' ability to treat cancer patients. Embodiments relate to a polynucleotide comprising a nucleic acid encoding a chimeric antigen receptor (CAR), a nucleic acid encoding an ODD domain, and a nucleic acid encoding one or multiple sequences of HRE. Embodiments relate to a vector comprising the polynucleotide. Embodiments relate to a cell comprising the vector. Embodiments relate to a composition comprising a population of cells, and the cell is a lymphocyte. Embodiments relate to lymphocytes that inhibit tumor cells of a subject having a form of cancer for use in a method, the method comprising administering an effective amount of the composition to the subject. Embodiments relate to a method for treating a subject having a form of cancer, the method comprising administering an effective amount of the composition to the subject.

Hypoxia or low oxygen concentration in the tumor microenvironment (Hypoxic tumor microenvironment) has widespread effects ranging from altered angiogenesis and lymphangiogenesis to tumor metabolism, growth, and therapeutic resistance in different cancer types. Embodiments relate to a method of promoting maintenance of a T cell population under hypoxic conditions, the method comprising: introducing the polynucleotide comprising a nucleic acid encoding an ODD domain and a nucleic acid encoding one or multiple sequences of HRE into a population of T cells; and allowing the population of T cells to be exposed to a hypoxic conditions, wherein the maintenance of the population of T cells is higher than that of a population of T cells without the nucleic acid encoding the ODD domain and the nucleic acid encoding the one or multiple sequences of HRE.

In embodiments, promoting maintenance of a T cell population under hypoxic conditions include maintaining the population of T cells, such as maintaining the total number of T cells so that there are sufficient number of T cells to function effectively in killing the tumor cells or inhibiting the growth of tumor cells.

In embodiments, the ODD domain comprises residues 532nd to 585th, 548th to 603rd or 557th to 574th of human HIF-1α.

In embodiments, the ODD domain comprises SEQ ID NO: 17, 19, or 27.

In embodiments, the one or multiple sequences of HRE comprise nine repeated sequences of HRE.

In embodiments, the CAR comprises SEQ ID NO: 6 and binds Fibroblast activation protein-α (FAP). In embodiments, the CAR comprises the SEQ ID NO: 25 and binds GCC. In embodiments, the CAR comprises the SEQ ID NO: 21 and binds CLDN18.2. In embodiments, the CAR comprises the SEQ ID NO: 23 and binds GPC3.

In embodiments, the CAR binds tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, CLDN18.2, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, or EGFR.

In embodiments, the CAR comprises an antigen binding domain, a transmembrane domain, and an intracellular signaling domain. In embodiments, the antigen binding domain binds GCC, TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Rα2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1. In embodiments, the intracellular signaling domain comprises a signaling domain, or a primary signaling domain and a co-stimulatory signaling domain, wherein the signaling domain and the co-stimulatory signaling domain comprises a functional signaling domain of a protein comprising one of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

In embodiments, the population of T cells is engineered to express and secrete a therapeutic agent such as a cytokine. In embodiments, the therapeutic agent is or comprises IL-6, or IFN-γ, or a combination thereof. In embodiments, the therapeutic agent is or comprises IL-15, or IL-12, or a combination thereof. In embodiments, the therapeutic agent is or comprises a recombinant or native, or naturally occurring cytokine. In embodiments, the population of T cells is derived from a healthy donor or a subject having cancer. In embodiments, the population of T cells has a reduced expression of the endogenous TRAC gene. In embodiments, the population of T cells comprises a first population of T cells comprising a first CAR binding a solid tumor antigen and a second population of T cells comprising a second CAR binding a white blood cell antigen. In embodiments, the white blood cell antigen is CD19, CD22, CD20, BCMA, CD5, CD7, CD2, CD16, CD56, CD30, CD14, CD68, CD11b, CD18, CD169, CD1c, CD33, CD38, CD138, or CD13. Embodiments relate to a polynucleotide comprising an NFAT promoter, a nucleotide sequence encoding a therapeutic agent, and a nucleotide sequence encoding a VHL-interaction domain (VHLD) of hypoxia-inducible factor 1-alpha (HIF-1α). Embodiments relate to a polynucleotide comprising a promoter corresponding to Hif-1α, NFAT, FOXP3, or NFkB, a nucleotide sequence encoding a therapeutic agent, and a nucleotide sequence encoding an oxygen-sensitive polypeptide domain. In embodiments, the therapeutic agent comprises at least one of IL-12, IL-6, IL-7, IL-15, IL-2, IL-23, GCSF, and GM-CSF.

Embodiments relate to a polynucleotide comprising an HRE nucleotide sequence, a nucleotide sequence encoding a therapeutic agent, and a nucleotide sequence encoding a VHLD of HIF-1α. The HRE sequence is recognized by the hypoxia-inducible factor-1a (HIF-1a), the main transcription factor recruited in hypoxia. Exemplary sequences of HRE are provided herein, for example in Table 2 (SEQ ID NOs: 1 and 11).

Embodiments relate to a kit comprising an effective amount of vector-free nucleic acids comprising the polynucleotide of any embodiments described herein to render a population of immune cells specific for a tumor antigen expressed on the surface of the cells of a subject.

Embodiments relate to a method of using the polynucleotides described herein, the method comprising providing a viral particle (e.g., AAV, lentivirus or their variants) comprising a vector genome, the vector genome comprising the polynucleotide and a polynucleotide encoding an antigen binding molecule, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity. In embodiments, the AAV preparation may include AAV vector particles, empty capsids, and host cell impurities, thereby providing an AAV product substantially free of AAV empty capsids.

Embodiments relate to a modified cell comprising the polynucleotides described herein. In embodiments, the modified cell comprises the antigen binding molecule. The antigen binding molecule is a CAR, which comprises an antigen binding domain, a transmembrane domain, and an intracellular signaling domain.

In embodiments, the oxygen-sensitive polypeptide domain comprises HIF-1α, HIF-3α, or a polypeptide comprising an amino acid sequence having a sequence identity of over 80%, 90%, or 95% with the HIF VHL-interaction domain (SEQ ID NO: 10), HIF amino acids 344-417, or HIF amino acid 380-603. In embodiments, the oxygen-sensitive polypeptide domain comprises the HIF VHL binding domain.

More information regarding the ODD domain of HIF-1α can be found in Harada et al. (Cancer Research, 2002, 62, 2013-2018) and Kosti et al. (Cell Reports Medicine, Apr. 20, 2021, 2, 100227), which are hereby incorporated by reference in their entirety.

In embodiments, the therapeutic agent comprises or is a cytokine. In embodiments, the therapeutic agent comprises or is IL-1P, IL-2, IL-4, IL-5, IL-6, IL-8, IL-10, IL-12, IL-13, IL-15, IL-17, IL-1Ra, IL-2R, IFN-γ, IFN-γ, MIP-In, MIP-IP, MCP-1, TNFα, GM-CSF, GCSF, CXCL9, CXCL10, CXCR factors, VEGF, RANTES, EOTAXIN, EGF, HGF, FGF-P, CD40, CD40L, ferritin, or any combination thereof. In embodiments, the cytokines include proinflammatory cytokines such as IFN-γ, IL-15, IL-4, IL-10, TNFα, IL-8, IL-5, IL-6, GM-CSF, MIP-Iα, or any combination thereof. In embodiments, the therapeutic agent comprises or is IL-12, IL-6, IL-7, IL-15, IL-23, GCSF, GM-CSF, or any combination thereof.

In embodiments, the modified cell comprises the antigen binding molecule. The antigen binding molecule is a modified TCR. In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, the cell is an immune cell (e.g., a population of immune effector cells). In embodiments, the immune cell is a T cell or an NK cell. In embodiments, the immune effector cell is a T cell. In embodiments, the T cell is a CD4+ T cell, a CD8+ T cell, or a combination thereof. In embodiments, the cell is a human cell.

In embodiments, the modified cell comprises a nucleic acid sequence encoding a binding molecule and a dominant negative form of an inhibitory immune checkpoint molecule or a receptor thereof. In embodiments, the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160. In embodiments, the inhibitory immune checkpoint molecule is modified PD-1. In embodiments, the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell.

Embodiments relate to a pharmaceutical composition comprising a population of modified cells and a population of additional modified cells, wherein the modified cells bind a first antigen, and the additional modified cells bind a second antigen, which is different from the first antigen. In embodiments, the first antigen is a white blood cell antigen, and the second antigen is a solid tumor antigen. In embodiments, the second antigen is a white blood cell antigen, and the first antigen is a solid tumor antigen. In embodiments, the white blood cell antigen is CD19, CD22, CD20, BCMA, CD5, CD7, CD2, CD16, CD56, CD30, CD14, CD68, CD11b, CD18, CD169, CD1c, CD33, CD38, CD138, or CD13.

In embodiments, the first antigen is CD205, CD19, CD20, CD22, or BCMA. In embodiments, the second antigen is a solid tumor antigen. Examples of the solid tumor antigen include tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, CLDN18.2, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, or EGFR.

In embodiments, the solid tumor antigen comprises tumor associated MUC1, ACPP, TSHR, GUCY2C, UPK2, CLDN18.2, PSMA, DPEP3, CXCR5, B7-H3, MUC16, SIGLEC-15, CLDN6, Muc17, PRLR, and FZD10.

Embodiments relate to a method of eliciting or enhancing T cell response, treating a subject in need thereof, or enhancing cancer treatment thereof, the method comprising administering an effective amount of the pharmaceutical composition herein. In embodiments, the solid tumor antigen is ACPP, and the cancer is the prostate.

In embodiments, the binding molecule and/or therapeutic agent is associated with a suicide gene. In embodiments, the polynucleotide comprises a suicide gene. In embodiments, the suicide gene is RQR8. "Suicide gene" is a nucleic acid coding for a product, wherein the product causes cell death by itself or in the presence of other compounds. A representative example of such a therapeutic nucleic acid (suicide gene) codes for thymidine kinase of herpes simplex virus (HSV-TK) or RQR8. Additional examples are the thymidine kinase of varicella-zoster virus and the bacterial gene cytosine deaminase, which can convert 5-fluorocytosine to the highly toxic compound 5-fluorouracil. Embodiments include a 136 amino acid marker/suicide gene for T-cells. The translated protein is stably expressed on the cell surface after retroviral transduction. It binds QBEND10 with equal affinity to full length CD34.

Further, the construct binds Rituximab, and the dual epitope design engenders highly effective complement-mediated killing. Due to the small size of the construct, it can easily be co-expressed with typical T cell engineering transgenes, such as T cell receptors or CARs and others, allowing facile detection, cell selection as well as deletion of cells in the face of unacceptable toxicity with off the shelf clinical-grade reagents/pharmaceuticals. More information on RQR8 and suicide gene can be found at EPO Patent Publication NO: EP2836511, which is incorporated here by reference.

It has been reported that clinical trials using IL-12 to treat cancer resulted in inadequate response and high toxicity. Thus, they were stopped (e.g., Motzer et al. in Journal of Interferon and Cytokine Research 21:257-263, 2001). The present disclosure provides a safe and effective therapy to treat cancer such as lymphoma using IL-12. For example, a method for treating a subject having lymphoma, enhancing the treatment thereof, enhancing anti-tumor activities in the subject, or enhancing T cell response in the subject, the method comprises: administering an effective amount of modified cells herein to the subject, wherein the modified cells comprise the polynucleotide comprising an NFAT promoter, a nucleotide sequence encoding therapeutic agent, and/or a nucleotide sequence encoding a VHL-interaction domain of HIF-1α, wherein the therapeutic agent comprises at least one of IL-12, the modified cells comprise a CAR or TCR binding CD19, CD20, and/or CD22. More information about CAR T cells can be found in U.S. application Ser. No. 16/439,901, which is incorporated herein by its reference.

Embodiments relate to a composition comprising a population of mixed cells. The mixed cells comprise a first population of cells comprises a first CAR binding a first antigen, and a second population of cells comprises a second CAR binding a second antigen, the first antigen comprising CD205, and the second antigen comprising a solid tumor antigen.

Embodiments relate to a method of enhancing the expansion of cells in a subject, the method comprising: administering an effective amount of a composition to the subject having a form of cancer expressing a tumor antigen, wherein the composition comprises a first population of cells comprising a first CAR binding a first antigen, and a second population of cells comprising a second CAR binding a second antigen, the first antigen comprising CD205 and the second antigen comprising a solid tumor antigen; and allowing the first and second population of cells to expand, wherein expansion of the second population of cells in the subject is enhanced as compared to a subject administered a composition comprising the second population of cells without the first population of cells.

CD205, also known as DEC-205, or Lymphocyte antigen 75 (LY75), is a protein encoded by the LY75 gene. CD205 is a type I C-type lectin receptor normally expressed on various APC and some leukocyte sub-populations, characterized by a cytoplasmic domain-containing protein motif crucial for endocytosis and internalization. CD205 is a surface multilectin receptor with a cytoplasmatic domain-containing protein motifs crucial for endocytosis and internalization upon ligation. In addition, CD205 is known to act as a surface receptor for apoptotic and necrotic cells, leading to antigen uptake and processing. CD205 is expressed in hematopoietic cells, mainly by antigen-presenting cells (APC), but also in other tissues, including solid tumors. CD205 presents a rapid internalization rate and a favorable profile in terms of differential expression between neoplastic and healthy tissues and is a good target for CoupledCAR® technology. More information on CD205 and its uses in treating cancer can be found at Gaudio et al. at doi.org/10.3324/haematol.2019.227215.

In embodiments, the first population of cells comprises T cells, NK cells, or dendritic cells, and the second population of cells comprises T cells, NK cells, or dendritic cells.

In embodiments, the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, MAGE A4, or EGFR.

In embodiments, the first and second CARs comprise an antigen binding domain, a transmembrane domain, a co-stimulatory domain, and a CD3 zeta domain. In embodiments, the co-stimulatory domain comprises the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that binds CD83, or a combination thereof. In embodiments, the first CAR comprises an scFv binding CD19, an intracellular domain of 4-1BB or CD28, and a CD3 zeta domain. The second CAR comprises an scFv binding tMUC1, an intracellular domain of 4-1BB or CD28, and a CD3 zeta domain.

In embodiments, the second population of cells comprises a lentiviral vector encoding the second CAR and a dominant negative form of PD-1. In embodiments, the first population of cells comprises a lentiviral vector encoding the first CAR and a therapeutic agent. In embodiments, the therapeutic agent comprises a cytokine. In embodiments, the cytokine is IL6 and/or IFN-γ. In embodiments, the cytokine is at least one of IL6, IL12, IL-2, TNF-α, or IFN-γ.

In embodiments, IL-2 is IL-2v (IL-2 Variant) comprising the amino acid sequence of IL2 and the Asp20Thr, Asn88Arg, and Gln126Asp mutations, which can eliminate the binding of IL2 to the CD25 receptor on Treg, reduce immunosuppression, and enhance anti-tumor activity.

In embodiments, the method further comprises treating the subject having solid tumor cancer. In embodiments, the solid tumor cancer is cholangiocarcinoma, pancreatic cancer, breast cancer, colorectal cancer, thyroid cancer, or prostate cancer. In embodiments, the solid tumor antigen is tMUC1. In embodiments, the solid tumor antigen is GUCY2C. In embodiments, the solid tumor antigen is TSHR. In embodiments, the solid tumor is CLND18.2. In embodiments, the solid tumor antigen is ACPP. In embodiments, the solid tumor antigen is MAGE A4. In embodiments, the first population of cells is T cells. In embodiments, the first population of cells is T cells or NK cells.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:

1. A polynucleotide comprising a nucleic acid encoding a therapeutic molecule and a nucleic acid encoding a VHL-interaction domain of hypoxia-inducible factor-1α (HIF-1α).
2. The polynucleotide of embodiment 1, wherein the polynucleotide further comprises one or multiple sequences of Hypoxia-Response Element (HRE).
3. The polynucleotide of embodiment 2, wherein the therapeutic molecule comprises an antigen binding molecule (e.g., a chimeric antigen receptor (CAR) or a TCR).
4. The polynucleotide of any of embodiments 1-3, wherein the VHL-interaction domain comprises an Oxygen-Dependent Degradation (ODD) domain.
5. The polynucleotide of embodiment 4, wherein the ODD domain is the residues $532^{nd}$ to $585^{th}$, $548^{th}$ to $603^{th}$ or $557^{th}$ to $574^{th}$ of human HIF-1α.
6. The polynucleotide of embodiment 4, wherein the ODD domain comprises the SEQ ID NO: 19 or 17.
7. A vector comprising the polynucleotide of any of embodiments 1-6.
8. A cell comprising the vector of embodiment 7.
9. A composition comprising of a population of cells of embodiment 8.
10. A method of treatment or use of a medicine, the method comprising administering an effective amount of the composition to a subject having a form of cancer.
11. A method of enhancing conditional regulation of HIF-1α on expression of a therapeutic molecule, the method comprising introducing a polynucleotide into a population of cells, the polynucleotide comprising an HRE, a nucleic acid encoding a therapeutic molecule, and a nucleic acid encoding a mini-ODD domain or three repeats of a mini-ODD domain; and allowing the cells exposed to a hypoxia environment, wherein the expression of the therapeutic molecule by the cells is lower than the expression of therapeutic molecule by cells comprising a polynucleotide comprising an HRE, the nucleic acid encoding the therapeutic molecule, and a nucleic acid encoding a wild type ODD domain.
12. The method of embodiment 11, wherein the mini-ODD domain the SEQ ID NO: 19 or 17.
13. The polynucleotide of any of embodiments 1-12, wherein the Hypoxia-Response Element comprises a HRE domain or multiple repeats of HRE domain (e.g., 9).
14. The polynucleotide of embodiment 12, wherein the VHL-interaction domain comprises Hif-1α, Hif-3α, or a polypeptide comprising an amino acid sequence having a sequence identity of over 80%, 90%, or 95% with respectively Hif-1α VHL-interaction domain, Hif-1α amino acid 344-417, or Hif-1α amino acid 380-603.
15. The polynucleotide of any of embodiments 1-14, wherein the polynucleotide comprises at least one of the SEQ ID NOs: 1, 11, 17, and 19.
16. A kit comprising an effective amount of vector-free nucleic acids comprising the polynucleotide of any preceding embodiments to render a population of immune cells specific for a tumor antigen expressed on the surface of the cells of a subject.
17. A method or use of polynucleotide, the method comprising providing a viral particle (e.g., AAV, lentivirus or their variants) comprising a vector genome, the vector genome comprising the polynucleotide and a polynucleotide encoding an antigen binding molecule, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity.
18. The method of embodiment 17, wherein the AAV preparation may include AAV vector particles, empty capsids, and host cell impurities, thereby providing an AAV product substantially free of AAV empty capsids.
19. A modified cell comprising the polynucleotide of any of embodiments 1-15.
20. The modified cell of embodiment 19, wherein the modified cell comprises a polynucleotide encoding a therapeutic agent.
21. The modified cell of embodiment 20, wherein the therapeutic agent comprises or is IL-1P, IL-2, IL-4, IL-5, IL-6, IL-8, IL-10, IL-12, IL-13, IL-15, IL-17, IL-1Ra, IL-2R, IFN-γ, IFN-γ, MIP-In, MIP-IP, MCP-1, TNFα, GM-CSF, GCSF, CXCL9, CXCL10, CXCR factors, VEGF, RANTES, EOTAXIN, EGF, HGF, FGF-P, CD40, CD40L, ferritin, and any combination thereof. In embodiments, the cytokines include proinflammatory cytokines such as IFN-γ, IL-15, IL-4, IL-10, TNFα, IL-8, IL-5, IL-6, GM-CSF, CCL19, and/or MIP-Iα.
22. The modified cell of embodiment 20, wherein the therapeutic agent comprises or is IL-12, IL-6, IL-7, IL-15, IL-23, GCSF, and/or GM-CSF
23. The polynucleotide, the method, or the modified cell of any of embodiments 1-22, wherein the therapeutic molecule is a CAR.
24. The polynucleotide, the method, or the modified cell of embodiment 23, wherein the CAR comprises an antigen binding domain, a transmembrane domain, and an intracellular signaling domain.
25. The polynucleotide, the method, or the modified cell of embodiment 24, wherein the antigen binding domain binds to a tumor antigen is selected from a group consisting of: GCC, TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

26. The polynucleotide, the method, or the modified cell of embodiment 24, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D 27. The polynucleotide, the method, or the modified cell of any of embodiments 1-22, wherein the therapeutic molecule is a modified TCR.

28. The polynucleotide, the method, or the modified cell of embodiment 27, wherein the TCR is derived from spontaneously occurring tumor-specific T cells in patients.

29. The polynucleotide, the method, or the modified cell of embodiment 27, wherein the TCR binds to a tumor antigen.

30. The polynucleotide, the method, or the modified cell of embodiment 27, wherein the tumor antigen comprises CEA, gp100, MART-1, p53, MAGE-A3, or NY-ESO-1.

31. The polynucleotide, the method, or the modified cell of embodiment 27, wherein the TCR comprises TCRγ and TCRδ Chains or TCRα and TCRβ chains, or a combination thereof.

32. The modified cell of any of the preceding embodiments, wherein the cell is an immune cell (e.g., a population of immune effector cells).

33. The modified cell of embodiment 32, wherein the immune cell is a T cell (γδT and/or αβT) or an NK cell.

34. The modified cell of embodiment 32, wherein the immune effector cell is a T cell.

35. modified cell of embodiment 32, wherein the T cell is a CD4+ T cell, a CD8+ T cell, or a combination thereof.

36. The modified cell of any of the preceding embodiments, wherein the cell is a human cell.

37. The modified cell of any proceeding embodiments, wherein the modified cell comprises a nucleic acid sequence encoding a binding molecule and a dominant negative form of an inhibitory immune checkpoint molecule or a receptor thereof.

38. The modified cell of embodiment 37, wherein the inhibitory immune checkpoint molecule is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160.

39. The modified cell embodiment 37, wherein the inhibitory immune checkpoint molecule is modified PD-1.

40. The modified cell of embodiment 39, wherein the modified PD-1 lacks a functional PD-1 intracellular domain for PD-1 signal transduction, interferes with a pathway between PD-1 of a human T cell of the human cells and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell.

41. The modified cell of any proceeding embodiments, wherein the modified cell is engineered to express and secrete a therapeutic agent such as a cytokine.

42. The modified cell of embodiment 41, wherein the therapeutic agent is or comprises IL-6 or IFN-γ, or a combination thereof.

43. The modified cell of embodiment 41, wherein the therapeutic agent is or comprises IL-15 or IL-12, or a combination thereof.

44 The modified cell of any of embodiments 41-43, wherein the therapeutic agent is or comprises a recombinant, native, or naturally occurring cytokine.

45 The modified cell of embodiment 44, wherein the small protein is or comprises IL-12, IL-6, or IFN-γ.

46. The modified cell of any proceeding embodiments, wherein the modified cell is derived from a healthy donor or the subject having cancer.

47. The modified cell of embodiment 46, wherein the modified ell has a reduced expression of endogenous TRAC gene.

48. The modified cell of any proceeding embodiments, wherein the modified cell comprises a first CAR binding a white blood antigen and a second CAR binding a solid tumor antigen.

49. The modified cell of any proceeding embodiments, wherein the modified cell comprises a bispecific CAR binding a white blood antigen and a solid tumor antigen.

50. A pharmaceutical composition comprising a population of the modified cells of any preceding suitable embodiments, wherein the modified cells bind a first antigen, and the additional modified cells bind a second antigen, different from the first antigen.

51. The pharmaceutical composition of embodiment 50, wherein the first antigen is a white blood cell antigen, and the second antigen is a solid tumor antigen.

52. The pharmaceutical composition of embodiment 50, wherein the second antigen is a white blood cell antigen, and the first antigen is a solid tumor antigen.

53. The pharmaceutical composition of any of embodiments 50-52, wherein the white blood cell antigen is CD19, CD22, CD20, BCMA, CD5, CD7, CD2, CD16, CD56, CD30, CD14, CD68, CD11b, CD18, CD169, CD1c, CD33, CD38, CD138, or CD13.

54. The pharmaceutical composition of any of embodiments 50-52, wherein is CD19, CD20, CD22, or BCMA.

55. The pharmaceutical composition of any of embodiments 50-54, wherein the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, CLDN18.2, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, or EGFR.

56. The pharmaceutical composition of any of embodiments 50-54, wherein the solid tumor antigen comprises tumor associated MUC1, ACPP, TSHR, GUCY2C, UPK2, CLDN18.2, PSMA, DPEP3, CXCR5, B7-H3, MUC16, SIGLEC-15, CLDN6, Muc17, PRLR, and FZD10.

57. A method of eliciting or enhancing T cell response, treating a subject in need thereof, or enhancing cancer treatment thereof, the method comprising administering an effective amount of the pharmaceutical composition of any of proceeding suitable embodiments.

58. A method for treating a subject having lymphoma, enhancing the treatment thereof, enhancing Anti-Tumor activities in the subject, or enhancing T cell response in the subject, the method comprising: administering an effective amount of modified cells of any preceding suitable embodiments to the subject, wherein the modified cells comprise the polynucleotide comprising an NFAT promoter, a nucleic acid encoding therapeutic agent, and/or a nucleic acid encoding a VHL-interaction domain of HIF-1α, wherein the therapeutic agent comprises at least one of IL-12, the modified cells comprise a CAR or TCR binding CD19, CD20, and/or CD22. More information about CART cells can be found in U.S. application Ser. No. 16/439,901, which is incorporated herein by its reference.

59. A method for enhancing the treatment of cancer using CAR T cells, enhancing the anti-tumor activity of CAR T cells in the subject, or enhancing T cell response in the subject, the method comprising: administering an effective amount of modified cells of any preceding suitable embodiments to the subject, wherein the modified cells comprise the polynucleotide comprising a HRE promoter, a nucleic acid encoding a CAR, and a nucleic acid encoding a VHL-interaction domain of HIF-1α, wherein the treatment, anti-tumor activity, and/or T cell response is greater than a subject administered with modified cells comprise a polynucleotide encoding a CAR in the hypoxic tumor microenvironment.

60. A method for enhancing the treatment of cancer using CAR T cells, enhancing the anti-tumor activity of CAR T cells in the subject, or enhancing T cell response in the subject, the method comprising: administering an effective amount of modified cells of any preceding suitable embodiments to the subject, wherein the modified cells comprise the polynucleotide comprising a HRE promoter and a nucleic acid encoding a CAR, wherein the treatment, anti-tumor activity, and/or T cell response is greater than a subject administered with modified cells comprise a polynucleotide encoding a CAR in the hypoxic tumor microenvironment.

61. A method for enhancing the treatment of cancer using CAR T cells, enhancing the anti-tumor activity of CAR T cells in the subject, or enhancing T cell response in the subject, the method comprising: administering an effective amount of modified cells of any preceding suitable embodiments to the subject, wherein the modified cells comprise the polynucleotide comprising a nucleic acid encoding a CAR, and a nucleic acid encoding a VHL-interaction domain of HIF-1α, wherein the treatment, anti-tumor activity, and/or T cell response is greater than a subject administered with modified cells comprise a polynucleotide encoding a CAR in the hypoxic tumor microenvironment.

62. The method of any of embodiments 59-61, wherein the modified cells comprise mixed CAR T cells described in ICT's PCT Publication Nos: WO2020106843 and WO2020146743, which are incorporated by their entirety.

63. A composition comprising a first population of cells targeting a solid tumor antigen and a second population of cells targeting the solid tumor antigen, wherein:

the first and second populations of cells comprise a first binding molecule binding the solid tumor antigen and are engineered such that expression of the first binding molecule in the first population of cells in the tumor microenvironment (TME) is less than the expression of the first binding molecule in the second population of cells in the TME, the first and second populations of cells comprise a first binding molecule binding the solid tumor antigen and are engineered such that the amount of the first binding molecule in the first population of cells is lower than the amount of the first binding molecule in the second population of cells in TME, and/or the first and second populations of cells comprise a first binding molecule binding the solid tumor antigen, activation of the first population of cells in the TME is less than activation of the second population of cells in the TME.

64. The composition of embodiment 63, wherein a ratio of the first population of cells to the second population of cells comprises a ratio from 1:1 to 1:$10^4$, or a ratio of 1:1, 1:10, 1:100, 1:1000, or 1:$10^4$.

65. The composition of embodiment 63, wherein a ratio of the first population of cells to the second population of cells comprises a ratio from 1:2 to 1:1000, or a ratio of 1:2, 1:3, 1:4, 1:5, 1:6, 1:7, 1:8, 1:9, 1:10, 1:100, or 1:1000.

66. The composition of embodiment 63, wherein a ratio of the first population of cells to the second population of cells comprises a ratio of less than 1:1 and more than 1:100.

67. The composition of embodiment 63, wherein a ratio of the first population of cells to the second population of cells comprises a ratio of less than 1:1 and more than 1:10.

68. The composition of any of embodiments 63-67, wherein the composition further comprises a third population of cells comprising a second binding molecule targeting a tumor associated antigen (TAA) and/or a tumor specific antigen (TSA) or the second binding molecule binds FAP or tMUC1.

69. The composition of embodiment 68, wherein the first binding molecule binds a solid tumor antigen of organ lineage antigens (OLAs).

70. The composition of any of embodiments 63-68, wherein the composition further comprises a fourth population of cells comprising a third binding molecule targeting a WBC antigen.

71. The composition of embodiment 70, wherein the WBC antigen comprises CD19, CD22, CD20, BCMA, CD5, CD7, CD2, CD16, CD56, CD30, CD14, CD68, CD11b, CD18, CD169, CD1c, CD33, CD38, CD138, FCRL5, CD13, or a combination thereof.

72. The composition of embodiment 70, wherein the WBC antigen comprises CD19, CD20, CD22, BCMA, or a combination thereof.

73. The composition of embodiment 70, wherein the WBC antigen comprises an antigen of a B cell.

74. The composition of any of embodiments 63-73, wherein the binding molecule is a chimeric antigen receptor (CAR) or a TCR.

75. The composition of embodiment 74, wherein the CAR comprises an antigen binding domain, a transmembrane domain, and an intracellular signaling domain.

76. The composition of embodiment 75, wherein the antigen binding domain binds a tumor antigen listed in Table 1.

77. The composition of embodiment 75 or 76, wherein the second population of cells comprises a CAR that comprises an antigen binding domain, a transmembrane domain, and an intracellular signaling domain, the intracellular signaling domain comprising a co-stimulatory signaling domain or a primary signaling domain and a co-stimulatory signaling domain, wherein the co-stimulatory signaling domain comprises a functional signaling domain of a protein comprises CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, or a combination thereof.

78. The composition of embodiment 74, wherein the antigen binding molecule comprises a modified TCR or a TCR.

79. The composition of embodiment 78, wherein the TCR is derived from spontaneously occurring tumor-specific T cells in a patient, and the TCR binds a tumor antigen.

80. The composition of embodiment 79, wherein the tumor antigen comprises CEA, gp100, MART-1, p53, MAGE-A3, NY-ESO-1, or a combination thereof.

81. The composition of embodiment 78, wherein the TCR comprises TCRγ and TCRδ chains, or TCRα and TCRβ chains, or a combination thereof.

82. The composition of any embodiment of embodiments 1-19, wherein the first, the second, and/or third population of cells comprise T cells or NK cells.

83. The composition of any embodiment of embodiments 1-19, wherein the first, the second, and/or third population of cells comprise T cells.

84. The composition of any embodiment of embodiments 1-21, wherein at least a portion of the first, the second, and/or third population of cells comprise a therapeutic agent.

85. The composition of embodiment 84, wherein the therapeutic agent comprises IL-12, IL-6, IFN-γ, or a combination thereof.

86. The composition of any of embodiments 63-85, wherein the second population of cells comprise the polynucleotide of any of embodiments 1-62.

87. The composition of embodiment 86, wherein the first population of cells does not comprise exogenous HRE or ODD domain.

88. The composition of embodiment 87, wherein the third population of cells does not comprise exogenous HRE or ODD (but can comprise HRE) domain.

89. The composition of embodiment 88, wherein the fourth population of cells does not comprise exogenous ODD domain.

90. The composition of embodiment 86, wherein the first population of cells does not comprise an exogenous polynucleotide comprising HRE and ODD domain.

91. The composition of embodiment 90, wherein the third population of cells does not comprise an exogenous polynucleotide comprising HRE and ODD domain.

92. The composition of embodiment 91, wherein the fourth population of cells does not comprise an exogenous polynucleotide comprising ODD domain (but can comprise HRE).

93. The composition of any of embodiments 63-92, wherein the TME is hypoxia, lower nutrient storage, and/or higher acidic pH.

94. The composition of embodiment 93, wherein the second, third, or fourth population of express one or more molecules at a level that is higher or lower than the level of the one or more expressed by a wild-type cell, wherein the one or more molecules are associated with the metabolism of the modified cell.

95. The composition of embodiment 94, wherein the modified cell comprises a disruption in an endogenous gene or addition of an exogenous gene that is associated with a biosynthesis or transportation pathway of one or more molecules.

96. The composition of embodiment 94 or 95, wherein the one more molecules comprise at least one of MCT1, MCT2, MCT3, LDHB, and MPC, a functional variant of the one or more molecules, or a functional fragment of the one or more molecules; and/or the metabolism comprises metabolism of lactic acid.

97. The composition of embodiment 94, wherein the metabolism comprises transportation of lactic acid of the modified cells, which is changed.

98. The composition of embodiment 94, wherein the modified cells transport less or more lactic acid into the modified cells than that of corresponding wild-type cells.

99. The composition of embodiment 94, wherein the modified cells overexpress MCT 3 and express less MCT1 and MCT2, and transport less lactic acid into the modified cells than that of corresponding wild-type cells.

100. The composition of embodiment 94, wherein the modified cells overexpress MCT1, MCT2, LDHB, and MPC, express less MCT3, and transport more lactic acid into the modified cells than that of corresponding wild-type cells.

101. The composition of embodiment 94, wherein the one more molecules comprise at least one of Frataxin, HBA, HBB, HBD, HBE, HBG, TOMM20, and TOMM22, a functional variant of the one or more molecules, or a functional fragment of the one or more molecules; and/or the metabolism comprises metabolism of lactic acid.

102. The composition of embodiment 94, wherein the metabolism comprises the oxidative function of mitochondria of the modified cells, which is enhanced.

103. The composition of embodiment 94, wherein the modified cells overexpress Frataxin, HBA, HBB, HBD, HBE, HBG such as to enhances the mitochondrial oxygen storage capacity of the modified cells.

104. The composition of embodiment 94, wherein the modified cells overexpress TOMM20 and TOMM22 such as to enhance the functions of mitochondria of the modified cells.

105. The composition of embodiment 94, wherein the one more molecules comprise at least one of CD98, SNAT1, SNAT2, ASCT2, a functional variant of the one or more molecules, or a functional fragment of the one or more molecules; and/or the metabolism comprises metabolism of amino acids.

106. The composition of embodiment 94, wherein the metabolism comprises the metabolism of the modified cells' lactic acid and/or amino acids, which is enhanced.

107. The composition of embodiment 94, wherein the modified cells overexpress CD98, SNAT1, SNAT2, and ASCT2 such as to enhances the transportation capability for the modified cells to transport the amino acids into the modified cells.

Table 2 provides exemplary sequences. Related sequences, compositions, and methods of treating cancer are provided in this Application and Innovative Cellular Therapeutics' PCT Patent Publication NOS: WO2016138846, WO2018126369, WO2017167217, WO2019140100, WO2020146743, WO2021216731, WO2020106843, WO2020047306, and WO2022150831 and US Patent Publication NOS: US20210060069 and US20210100841, which are incorporated by reference in their entirety.

TABLE 2

Sequences and corresponding sequence identifiers

| SEQ ID NO | ID |
|---|---|
| 1 | 9*HRE (EPO) |
| 2 | IL2 promoter |
| 3 | CD8sp DNA |
| 4 | CD8sp aa |
| 5 | FAP scFv 1 (Example) DNA |
| 6 | FAP scFv 1 (Example) aa |
| 7 | 4-1BB DNA |
| 8 | 4-1BB AA |
| 9 | ODD domain DNA |
| 10 | ODD domain AA |
| 11 | 5*HRE (epo) |
| 12 | 5*HRE (VEGF) |
| 13 | EF-1A |
| 14 | FAP scfv 2 |
| 15 | EA |
| 16 | 3x mini ODD domain DNA |
| 17 | 3x mini ODD domain AA |
| 18 | 2x mini ODD domain DNA |
| 19 | 2x mini ODD domain AA |
| 20 | CLDN18.2 scfv DNA |
| 21 | CLDN18.2 scfv AA |
| 22 | GPC3 scfv DNA |
| 23 | GPC3 scfv AA |
| 24 | Linker |
| 25 | GCC scFv |
| 26 | 1x mini ODD domain DNA |
| 27 | 1x mini ODD domain AA |

EXAMPLES

Lentiviral vectors that encode individual CAR molecules were generated and transfected with T cells, which are discussed below. In addition, techniques related to cell cultures and the construction of cytotoxic T lymphocyte assay may be found in "Control of large, established tumor xenografts with genetically retargeted human T cells containing CD28 and CD137 domains," PNAS, Mar. 3, 2009, vol. 106 no. 9, 3360-3365 and "Chimeric Receptors Containing CD137 Signal Transduction Domains Mediate Enhanced Survival of T Cells and Increased Antileukemic Efficacy In Vivo," Molecular Therapy, August 2009, vol. 17 no. 8, 1453-1464, which are incorporated herein by reference in its entirety.

Figure 2:
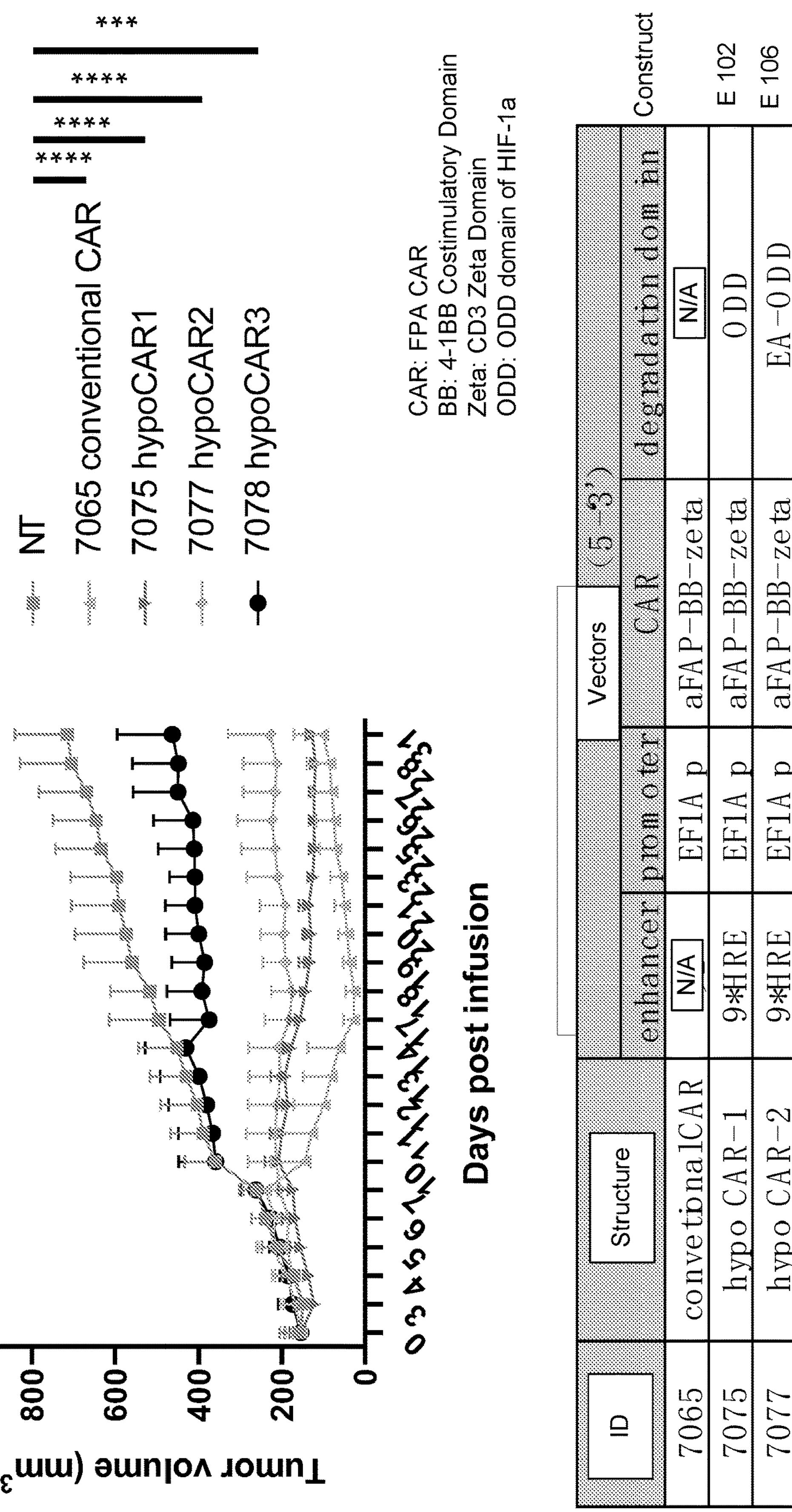
FIG. 2 shows the anti-tumor effect of various CAR T cells.
Figure 3:
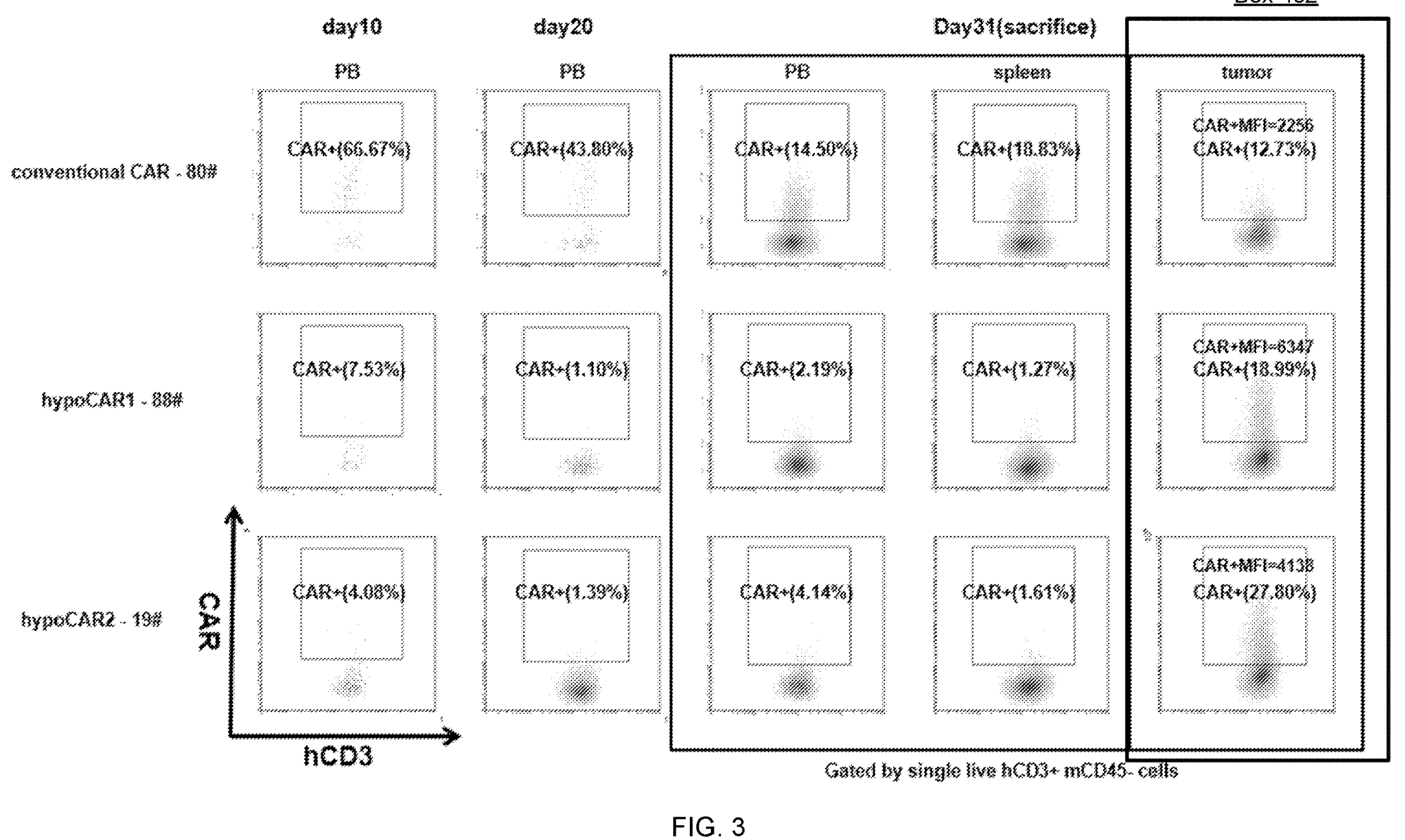
FIG. 3 shows flow cytometry results of the expression of CAR T cells in the mice's peripheral, spleens, and tumors on days 10, 20, and 31, respectively.

In vivo and In vitro experiments were performed to test the expression and functions of the hypoxia enhanced FAP CAR (hypo FAP CAR) T cells targeting FAP (See Constructs in FIG. 1: E102 and E106 and FAP scFv: SEQ ID NO: 6). Hypo FAP CARs' expression and functions (e.g., cytokine release and killing ability) under normal conditions are similar to conventional FAP CAR (without regulation of HRE and ODD domain). However, activation of CAR T cells under hypoxia is significantly less than conventional CAR T cells, and CD4+ CAR T cells are more susceptible to hypoxia than CD8+ CAR T cells. The hypo FAP CAR has limited expression, which may reduce the on-target off-tumor cytotoxicity. Since FAP is widely expressed in tumors and is an ideal target to clear tumor stromal cells, hypo FAP CAR T cells may be better adapted to the hypoxic tumor environment. As for the in vivo experiments, JIM IT-1 mice model was established to overexpress FAP. On day 0, the mice were infused with hypo CAR T and conventional CAR T cells. On day 5, the peripheral blood samples were collected from the mice. On day 31, the mice were sacrificed to measure CAR expression and/or tumor sizes in the peripheral blood, spleen, and tumors. FIG. 2 shows the anti-tumor effect of various CAR T cells. As shown, the anti-tumor effect of hypo CAR T cells is significantly greater than those of non-transduced T cells. Also, hypo CAR-1 T cells (E 102) show a better anti-tumor effect than the other hypo CAR T cells. FIG. 3 shows flow cytometry results of expression of CART cells in the mice's peripheral, spleens, and tumors on days 10, 20, and 31, respectively. As shown, there is little CAR T cell expression in peripheral blood.

Further, compared with T cells expressing conventional FAP CAR, CAR T cells expressing hypoxia elements and FAP CAR (hypo FAP CAR) appear to be maintained inside the tumor for a longer time (See Box 402 of FIG. 3) than that of conventional FAP CAR T cells. These results demonstrate that the expression of FAP CARs under hypoxic conditions is significantly reduced, and hypo FAP CAR T cells may be used to reduce the on-target off-tumor cytotoxicity. Also, it is surprising that hypo CAR T cells have enhanced anti-tumor effects in the hypoxic tumor microenvironment compared to conventional CAR T cells, given that hypoxia elements were originally designed to restrict CAR expression in the hypoxic microenvironment for safety concerns. These results show that enhanced hypoxia elements not only make CAR T cells safer but also enhance CAR T cells' response (the maintenance of CAR T cell population) in the tumor microenvironment environment (TME).

Figures 5A, 5B, 5C:
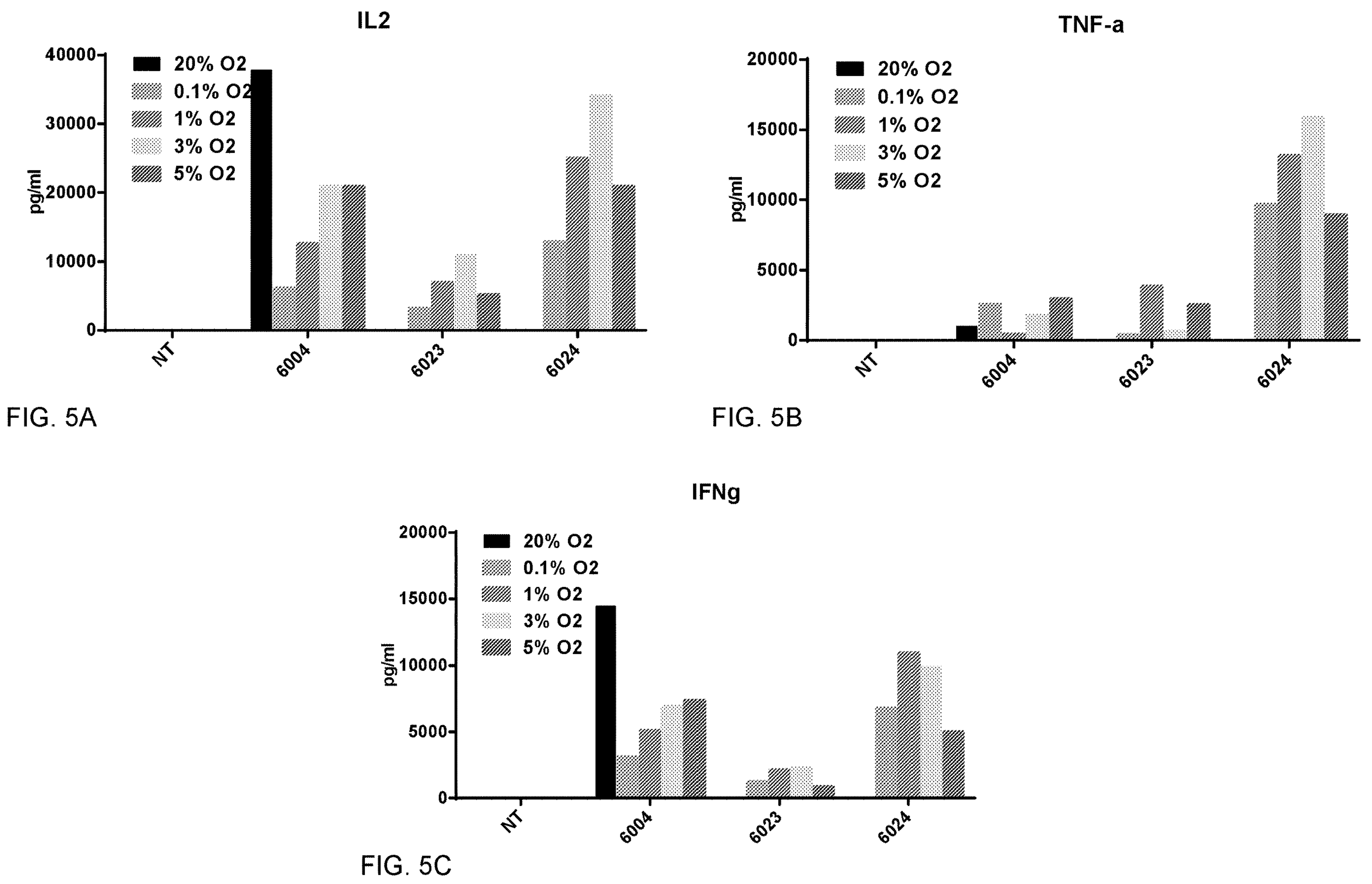
FIGS. 5A, 5B, and 5C show cytokine release by CAR T cells expressing hypo CLDN18.2 CARs and conventional CLDN18.2 CAR when co-cultured with substrate cells.

Hypo CAR targeting other tumor markers was also studied. Two hypo CLDN18.2 CAR T cells were designed and generated (i.e., 6023 and 6024 in FIG. 4). CAR expression in CAR T cells 6004 (control, without ODD domain), 6023 (full-length ODD), and 6024 (3× mini ODD) were measured in normoxia and hypoxia using flow cytometry. The killing effect of CAR T cells 6023 and 6024 gradually weakens with the increase of oxygen concentration, and the safety and killing effect of the two CAR T cells are similar, while the killing effect of the control CAR T cells remains higher than CAR T cells 6023 and 6024. Under hypoxic conditions, CAR T cells 6024 released more cytokine than CAR T cells 6023 under hypoxic conditions, a surprising discovery. Even under hypoxic conditions, when the cells are weakened, the 6024 CAR T cells can release similar or higher amounts of cytokines as compared to control cells, CAR T 6004, and can release more cytokines than CAR T cells 6023 with the full-length ODD domain. FIG. 4 shows structures of hypo CLDN18.2 CARs and the killing ability of T cells expressing these hypo CLDN18.2 CARs and conventional CLDN18.2 CAR when co-cultured with substrate cells. FIG. 5A-5C show cytokine release by CAR T cells expressing hypo CLDN18.2 CARs and conventional CLDN18.2 CAR when co-cultured with substrate cells.

Figure 7:
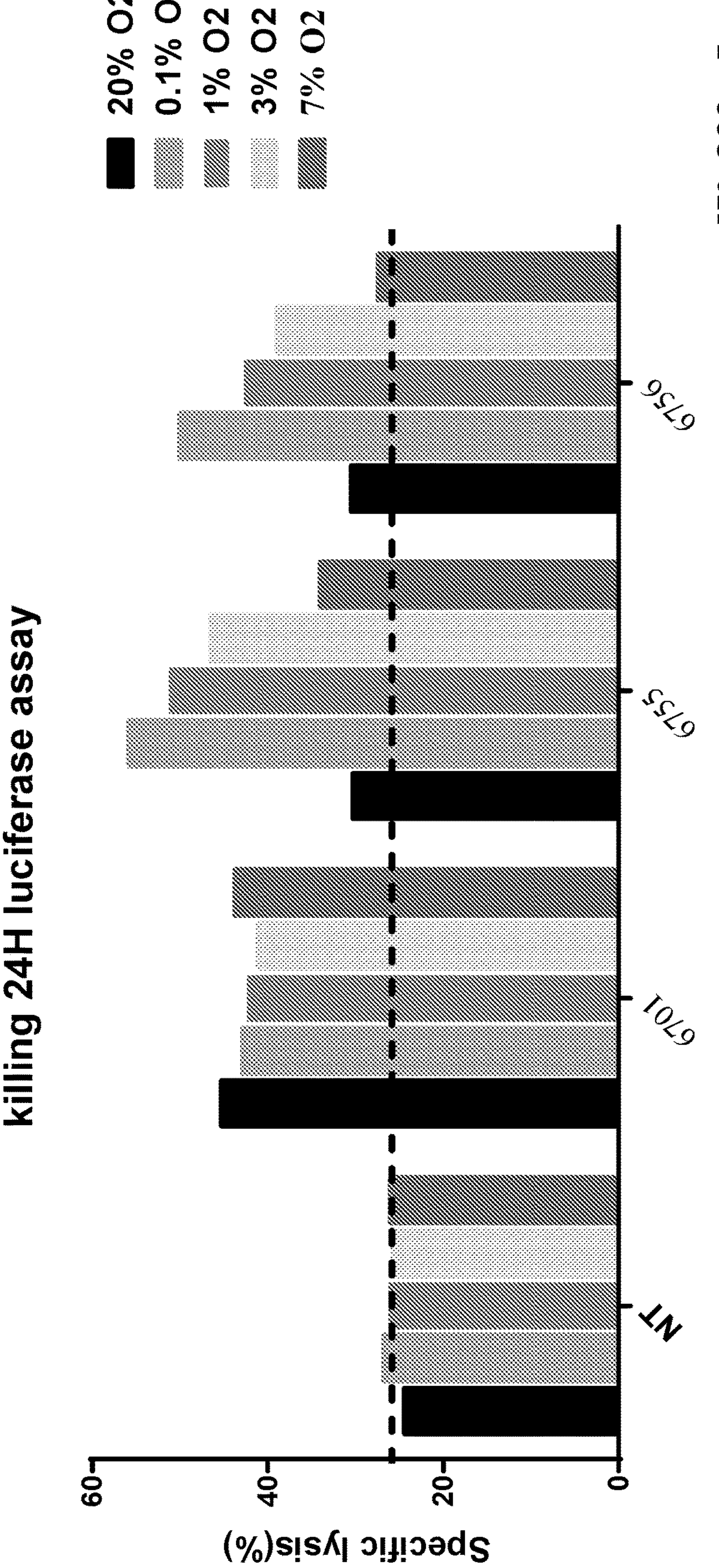
FIG. 7 shows the structures of hypo GCC CARs and the killing ability of T cells expressing these hypo GCC CARs and conventional GCC CAR when co-cultured with substrate cells. "GUCY2C" refers to GUCY2C scFv. "LV" refers to lentiviral vector. "9×HRE" is shown in SEQ ID NO: 1 (HRE repeated 9×). "BBZ" or "bbz" refers 4-1BB and CD3 zeta. "ODD" refers to the full length oxygen dependent degradation domain (SEQ ID NO: 10). "MiniODD" refers to a portion of ODD (SEQ ID NO: 27) repeated 3×.
Figures 8A, 8B, 8C, 8D:
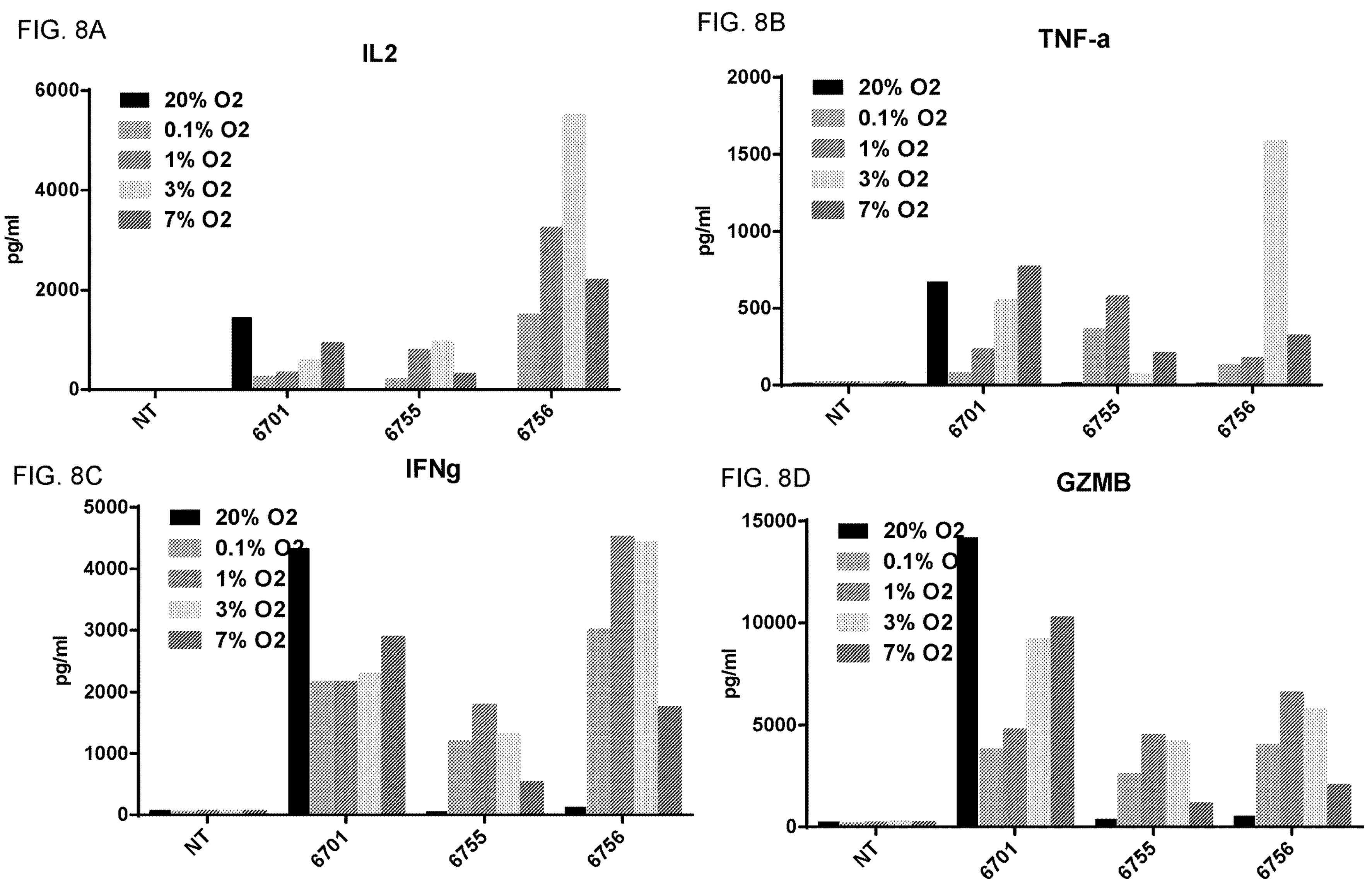
FIGS. 8A, 8B, 8C, and 8D show cytokine release by CAR T cells expressing hypo GUCY2C CARs and conventional GUCY2C CAR when co-cultured with substrate cells.

Similar results were found for other tumor markers (GPC3 and GCC). FIG. 6A-6C show structures of hypo GPC3 CARs and cytokine release by CAR T cells expressing hypo GPC3 CARs and conventional GPC3 CAR when co-cultured with substrate cells. FIG. 7 shows structures of hypo GCC CARs and the killing ability of T cells expressing these hypo GCC CARs and conventional GCC CAR when co-cultured with substrate cells. Finally, FIG. 8A-8D show cytokine release of CAR T cells expressing hypo GCC CARs and conventional GCC CAR when co-cultured with substrate cells. These results are surprising because hypo CAR T cells with 3× mini-ODD domain released more cytokines than those hypo CAR T cells with the full-length ODD domain under hypoxic conditions.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A method of maintaining a population of T cells expressing a chimeric antigen receptor (CAR) under hypoxic conditions, the method comprising: introducing a polynucleotide comprising a nucleic acid encoding an Oxygen-Dependent Degradation domain (ODD) comprising SEQ ID NO: 17 and a nucleic acid comprising one or more sequences of Hypoxia-Response Element (HRE) and a nucleic acid encoding the CAR into a population of T cells; and exposing the population of T cells to a hypoxic condition, wherein maintenance of the population of T cells is higher than that of a population of T cells without the nucleic acid encoding the ODD and the nucleic acid comprising one or more sequences of HRE.

2. The method of claim 1, wherein the one or more sequences comprise nine repeated sequences of HRE.

3. The method of claim 2, wherein the one or more sequences comprise SEQ ID NO: 1.

4. The method of claim 3, wherein the CAR comprises SEQ ID NO: 6 and binds Fibroblast activation protein-α (FAP).

5. The method of claim 3, wherein the CAR comprises SEQ ID NO: 25 and binds guanylyl cyclase 2C (GUCY2C) or GCC.

6. The method of claim 3, wherein the CAR comprises SEQ ID NO: 21 and binds CLDN18.2.

7. The method of claim 3, wherein the CAR comprises SEQ ID NO: 23 and binds GPC3.

8. The method of claim 3, wherein the CAR binds to tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, CLDN18.2, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, or EGFR.

9. The method of claim 3, wherein the CAR comprises an antigen binding domain, a transmembrane domain, and an intracellular signaling domain.

10. The method of claim 9, wherein the antigen binding domain binds to GCC, TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, Lewis Y, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, ETV6-AML, sperm protein 17, XAGE1, Tie 2, MAD-CT-1, MAD-CT-2, Fos-related antigen 1, p53, p53 mutant, prostein, survivin, PCTA-1/Galectin 8, MelanA/MART1, Ras mutant, ML-IAP, TMPRSS2-ERG fusion protein, NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase (hTERT), RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, or IGLL1.

11. The method of claim 9, wherein the intracellular signaling domain comprises a signaling domain, or a primary signaling domain and a co-stimulatory signaling domain, and wherein the signaling domain or co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

12. The method of claim 3, wherein the population of T cells is engineered to express and secrete a therapeutic agent, and optionally wherein the therapeutic agent is a cytokine.

13. The method of claim 12, wherein the therapeutic agent comprises IL-6 or IFN-γ, or a combination thereof.

14. The method of claim 12, wherein the therapeutic agent comprises IL-15 or IL-12, or a combination thereof.

15. The method of claim 12, wherein the therapeutic agent is or comprises a recombinant or naturally occurring cytokine.

16. The method of claim 3, wherein the population of T cells is derived from a healthy donor or a subject having cancer.

17. The method of claim 3, wherein the population of T cells has a reduced expression of endogenous TRAC gene.

18. The method of claim 3, wherein the population of T cells further comprises an additional CAR binding a white blood cell antigen.

19. The method of claim 18, wherein the white blood cell antigen is CD19, CD22, CD20, BCMA, CD5, CD7, CD2, CD16, CD56, CD30, CD14, CD68, CD11b, CD18, CD169, CD1c, CD33, CD38, CD138, or CD13.

* * * * *